United States Patent
Levine et al.

(10) Patent No.: US 11,655,383 B2
(45) Date of Patent: May 23, 2023

(54) PHOTOCHROMIC COMPOSITIONS, MARKERS CONTAINING THE SAME, AND SYSTEMS AND METHODS FOR THEIR USE

(71) Applicant: JADS INTERNATIONAL LLC, Lutherville, MD (US)

(72) Inventors: Andrew Seth Levine, Lutherville, MD (US); Nicole Ann Zujovic, Baltimore, MD (US); Debora Hense, Plymouth, MI (US)

(73) Assignee: JADS INTERNATIONAL LLC, Lutherville, MD (US)

( * ) Notice: Subject to any disclaimer, the term of this patent is extended or adjusted under 35 U.S.C. 154(b) by 995 days.

(21) Appl. No.: 16/279,125

(22) Filed: Feb. 19, 2019

(65) Prior Publication Data

US 2019/0284406 A1    Sep. 19, 2019

Related U.S. Application Data

(63) Continuation-in-part of application No. PCT/US2017/047751, filed on Aug. 21, 2017.
(Continued)

(51) Int. Cl.
*C09D 11/00* (2014.01)
*C09D 11/17* (2014.01)
(Continued)

(52) U.S. Cl.
CPC ............. *C09D 11/17* (2013.01); *A61K 8/72* (2013.01); *A61K 8/8152* (2013.01); *A61K 8/87* (2013.01);
(Continued)

(58) Field of Classification Search
CPC . C09D 1/00; C09D 11/00; C09D 4/00; C09D 5/00; C09D 11/17; C09D 11/50;
(Continued)

(56) References Cited

U.S. PATENT DOCUMENTS 3,787,687 A   1/1974  Trumble
3,903,423 A   9/1975  Zweig
(Continued)

FOREIGN PATENT DOCUMENTS

CN     202075232 U  *  12/2011
CN     202075232 U     12/2011
WO      02/03949 A2     1/2002

OTHER PUBLICATIONS

ISR_for_International_Application_No. PCT/US2017/047751.

*Primary Examiner* — James E McDonough
(74) *Attorney, Agent, or Firm* — Ladas & Parry LLP

(57) ABSTRACT

An ink composition including at least one photochromic pigment or dye, at least one film-forming resin, and at least one solvent in which the at least one photochromic pigment or dye and the at least one film-forming resin are dispersible or dissolvable, wherein the components of the ink composition are present in respective amounts such that the ink composition is in the form of a liquid or gel until evaporation of the at least one solvent, and wherein, upon evaporation of the at least one solvent, the at least one film-forming resin forms a film that (a) inhibits the ink composition from degrading when covered with the sunscreen product or (b) inhibits the ink composition from washing off when the sunscreen is washed off or both, the film-forming resin including shellac, polyurethane, acrylic polymer, silicone polymer or a mixture thereof.

18 Claims, 48 Drawing Sheets

| Product | Description | Form | Manufacturer |
|---|---|---|---|
| Avalure Flex-6 Polymer | Polyurethane | Powder | Lubrizol |
| Dow MQ-1640 | Trimethylsiloxy silicate & Polypropyl Silsesquioxane | Flake Resin | Dow Corning |
| Epitex 66 | Polyacrylate Emulsion | White Liquid | Dow Chemical Co. |
| Polysoleil SY400 | Shellac | Powder | Mantrose-Haeuser Co. |
| Silsoft Gel | Silicone | Gel | Momentive |
| Silsoft ETS | Ethyl Trisiloxane | Clear Liquid | Momentive |

Related U.S. Application Data

(60) Provisional application No. 62/377,033, filed on Aug. 19, 2016.

(51) Int. Cl.
| | | |
|---|---|---|
| *C09D 11/50* | (2014.01) | |
| *A61K 8/72* | (2006.01) | |
| *A61K 8/87* | (2006.01) | |
| *A61Q 1/02* | (2006.01) | |
| *A61K 8/81* | (2006.01) | |
| *C09D 1/00* | (2006.01) | |
| *C09D 4/00* | (2006.01) | |
| *C09D 5/00* | (2006.01) | |
| *G01N 21/29* | (2006.01) | |

(52) U.S. Cl.
CPC .............. *A61Q 1/025* (2013.01); *C09D 11/50* (2013.01); *A61K 2800/438* (2013.01); *G01N 21/29* (2013.01)

(58) Field of Classification Search
CPC ........ A61K 8/72; A61K 8/81582; A61K 8/87; A61K 2800/438; A61Q 1/025; G01N 21/29
USPC ........................ 106/31.01, 31.13, 31.6, 31.68
See application file for complete search history.

(56) References Cited

U.S. PATENT DOCUMENTS

| | | |
|---|---|---|
| 4,659,649 A | 4/1987 | Dickinson et al. |
| 5,117,116 A | 5/1992 | Bannard et al. |
| 5,296,275 A | 3/1994 | Goman et al. |
| 5,523,075 A | 6/1996 | Fuerst et al. |
| 5,581,090 A | 12/1996 | Goudjil |
| 5,589,398 A | 12/1996 | Krause et al. |
| 5,612,541 A | 3/1997 | Hoffmann et al. |
| 5,986,273 A | 11/1999 | Tripp et al. |
| 6,132,681 A | 10/2000 | Faran et al. |
| 6,504,161 B1 | 1/2003 | Jackson et al. |
| 6,531,118 B1 * | 3/2003 | Gonzalez ............... A61Q 5/00 424/59 |
| 6,734,440 B2 | 5/2004 | Questel et al. |
| 6,818,904 B1 | 11/2004 | Ferren et al. |
| 2001/0019110 A1 | 9/2001 | Faran et al. |
| 2002/0022008 A1 | 2/2002 | Forest et al. |
| 2004/0109789 A1 | 6/2004 | Faran et al. |
| 2005/0285050 A1 | 12/2005 | Bruce et al. |
| 2006/0067896 A1 | 3/2006 | Shaffer |
| 2011/0269850 A1 * | 11/2011 | Signorino ............ A61K 9/282 514/778 |
| 2012/0137958 A1 | 6/2012 | Mills et al. |
| 2012/0288690 A1 | 11/2012 | Forsythe |
| 2013/0177703 A1 | 7/2013 | Clayton et al. |
| 2014/0348757 A1 * | 11/2014 | Barrie ..................... A61K 8/34 424/59 |
| 2016/0017162 A1 | 1/2016 | Clayton et al. |

* cited by examiner

FIG. 1

| Product | Description | Form | Manufacturer |
|---|---|---|---|
| Avalure Flex-6 Polymer | Polyurethane | Powder | Lubrizol |
| Dow MQ-1640 | Trimethylsiloxy silicate & Polypropyl Silsesquioxane | Flake Resin | Dow Corning |
| Epitex 66 | Polyacrylate Emulsion | White Liquid | Dow Chemical Co. |
| Polysoleil SY400 | Shellac | Powder | Mantrose-Haeuser Co. |
| Silsoft Gel | Silicone | Gel | Momentive |
| Silsoft ETS | Ethyl Trisiloxane | Clear Liquid | Momentive |

FIG. 2

| # | Description | Type |
|---|---|---|
| 1 | Coppertone Kids Broad Spectrum SPF50 | Spray |
| 2 | Equate Sport Broad Spectrum SPF30 | Spray |
| 3 | Hawaiian Tropic Island Sport | Spray |
| 4 | Banana Boat Kids | Spray |
| 5 | Banana Boat Sport Coolzone | Spray |
| 6 | Banana Boat Sport SPF 50 | Lotion |
| 7 | Coppertone Sport SPF30 | Lotion |

FIG. 3

| # | Description | Avalure Flex-6 in Water | Dow MQ-1640 in Xiameter | Epitex 66 | Polysoleil SY400 in DA | Blue in Polysoleil SY400 on Simulated Skin |
|---|---|---|---|---|---|---|
| 1 | Coppertone Kids Broad Spectrum SPF50 (Spray) | Severe | Severe | Severe | Very Slight | Slight |
| 2 | Equate Sport Broad Spectrum SPF30 (Spray) | Severe | Severe | Severe | Very Slight | Slight |
| 3 | Hawaiian Tropic Island Sport (Spray) | Severe | Severe | Severe | No Effect | No Effect |
| 4 | Banana Boat Kids (Spray) | Severe | Severe | Severe | Slight | Very Slight |
| 5 | Banana Boat Sport coolzone (Spray) | Severe | Severe | Severe | Slight | Very Slight |
| 6 | Banana Boat Sport SPF 50 (Lotion) | Severe | Moderate | Severe | No Effect | No Effect |
| 7 | Coppertone Sport SPF30 (Lotion) | Severe | Moderate | Severe | No Effect | No Effect |

FIG. 4

| Brand No. | Coppertone Description | SPF |
|---|---|---|
| 1 | Water Babies (lotion & stick) | 50 & 55 |
| 2 | Kids (lotion & stick) | 50 & 55 |
| 3 | Ultra Guard | 30 & 50 |
| 4 | Sport (lotions & stick) | 15, 30, 50 & 55 |
| 5 | Clearly Sheer | 30 & 50 |
| 6 | Tanning Lotion | 4, 8 & 15 |
| 7 | Tanning Oil | 15 |
| 8 | Oil-Free Faces | 30 |

FIG. 5

| # | Coppertone Description | SPF | Color Return on Reactivation | |
|---|---|---|---|---|
| | | | 175A Blue Ink | 177B Pink Ink |
| 1-50 | Water Babies Lotion | 50 | Slight | No Effect |
| 1-55 | Water Babies Stick | 55 | No Effect | Slight |
| 2-50 | Kids Lotion | 50 | No Effect | No Effect |
| 2-55 | Kids Stick | 55 | Slight | Slight |
| 3-30 | Ultra Guard Lotion | 30 | No Effect | No Effect |
| 3-50 | Ultra Guard Lotion | 50 | No Effect | Slight |
| 4-15 | Sport Lotion | 15 | Slight | Slight |
| 4-30 | Sport Lotion | 30 | No Effect | Slight |
| 4-50 | Sport Lotion | 50 | Slight | Slight |
| 4-55 | Sport Stick | 55 | No Effect | No Effect |
| 5-30 | Clearly Sheer Lotion | 30 | Slight | No Effect |
| 5-50 | Clearly Sheer Lotion | 50 | Slight | Slight |
| 6-4 | Tanning Lotion | 4 | No Effect | No Effect |
| 6-8 | Tanning Lotion | 8 | No Effect | No Effect |
| 6-15 | Tanning Lotion | 15 | No Effect | No Effect |
| 7-15 | Tanning Oil | 30 | No Effect | No Effect |
| 8-30 | Oil-Free Faces | 50 | No Effect | No Effect |

FIG. 6

| No. | Description |
|---|---|
| 1 | Lip Gloss Bottle with Sponge Stick Applicator |
| 2 | Nail Polish Bottle with Brush Applicator |
| 3 | Bottle with Roller Ball Applicator |
| 4 | Dauber Bottle with Sponge Stamp Applicator |
| 5 | Alcohol Blending Pen with Wide Fiber Applicator |
| 6 | Viscot Fiber Marker Applicator Chisel Tip |

FIG. 7A

| Brand No. | Coppertone Description | SPF | Top 3 Ingredients | Active Ingredients |
|---|---|---|---|---|
| 1 | Water Babies (lotion) | 50 | Water<br>Propylene Glycol<br>C12-15 Alkyl Benzoate | Octinoxate (7.5%)<br>Octisalate (5%)<br>Zinc Oxide (14.5%) |
| 1 | Water Babies (stick) | 55 | Beeswax<br>Lauryl Laurate<br>Ozokerite | Avobenzone (3%)<br>Homosalate (15%)<br>Octisalate (5%)<br>Octocrylene (10%)<br>Oxybenzone (6%) |
| 2 | Kids (lotion) | 50 | Water<br>Propylene Glycol<br>C12-15 Alkyl Benzoate | Octinoxate (7.5%)<br>Octisalate (5%)<br>Zinc Oxide (14.5%) |
| 2 | Kids (stick) | 55 | Beeswax<br>Lauryl Laurate<br>Ozokerite | Avobenzone (3%)<br>Homosalate (15%)<br>Octisalate (5%)<br>Octocrylene (10%)<br>Oxybenzone (6%) |
| 3 | Ultra Guard | 30 | Water<br>Sorbitol<br>Ethylhexyl Palmitate | Avobenzone (3%)<br>Homosalate (10%)<br>Octisalate (5%)<br>Octocrylene (10%) |
| 3 | Ultra Guard | 50 | Water<br>Sorbitol<br>Aluminum Starch Octenylsuccinate | Avobenzone (3%)<br>Homosalate (13%)<br>Octisalate (5%)<br>Octocrylene (7%)<br>Oxybenzone (4%) |

FIG. 7 B

| | | | |
|---|---|---|---|
| 4 | Sport (lotion) | 15 | Water<br>Aluminum Starch Octenylsuccinate<br>Glycerin | Avobenzone (2%)<br>Homosalate (5%)<br>Octisalate (4.5%)<br>Octocrylene (3%) |
| | Sport (lotion) | 30 | Water<br>Aluminum Starch Octenylsuccinate<br>Glycerin | Avobenzone (3%)<br>Homosalate (8%)<br>Octisalate (4.5%)<br>Octocrylene (6%) |
| | Sport (lotion) | 50 | Water<br>Aluminum Starch Octenylsuccinate<br>Styrene/ Acrylates Copolymer | Avobenzone (3%)<br>Homosalate (10%)<br>Octisalate (4.5%)<br>Octocrylene (8%) |
| | Sport (stick) | 55 | Beeswax<br>Lauryl Laurate<br>Ozokerite | Avobenzone (3%)<br>Homosalate (15%)<br>Octisalate (5%)<br>Octocrylene (10%)<br>Oxybenzone (6%) |
| 5 | Clearly Sheer | 30 | Water<br>Aluminum Starch Octenylsuccinate<br>Ethylhexyl Isononanoate | Avobenzone (3%)<br>Homosalate (10%)<br>Octisalate (4.55%)<br>Octocrylene (8%) |
| | Clearly Sheer | 50 | Water<br>Aluminum Starch Octenylsuccinate<br>Dimethicone | Avobenzone (3%)<br>Homosalate (10%)<br>Octisalate (4.55%)<br>Octocrylene (9%)<br>Oxybenzone (5%) |

FIG. 7 C

| | | | | |
|---|---|---|---|---|
| 6 | Tanning Lotion | 4 | Water<br>Ethylhexyl Palmitate<br>Propylene Glycol | Octinoxate (3%)<br>Octocrylene (2%) |
| | Tanning Lotion | 8 | Water<br>Sorbitol<br>Ethylhexyl Palmitate | Octinoxate (7%)<br>Octocrylene (3%) |
| | Tanning Lotion | 15 | Water<br>Sorbitol<br>Ethylhexyl Palmitate | Avobenzone (2%)<br>Homosalate (10%)<br>Octisalate (5%)<br>Octocrylene (5%) |
| 7 | Tanning Oil | 15 | Isopropyl Palmitate<br>Cyclopentasiloxane<br>Mineral Oil | Avobenzone (2%)<br>Homosalate (10%)<br>Octisalate (4.5%)<br>Oxybenzone (3%) |
| 8 | Oil-Free Faces | 30 | Water<br>Sorbitol<br>Aluminum Starch Octenylsuccinate | Avobenzone (2%)<br>Homosalate (13%)<br>Octisalate (5%)<br>Octocrylene (2%)<br>Oxybenzone (4%) |

FIG. 8

| Product | Poly-Soleil SY 400 | Crystalc Premium Flake 500 | R-49 Refined Bleached Shellac | SSB Komet 58 Flake | Baycusan C 2000 |
|---|---|---|---|---|---|
| Manufacturer | | Mantrose-Hauser Co. | | | Covestro |
| Description | Shellac | Shellac | Shellac | Shellac | Polyurethane |
| Form | Powder | Thin Flakes | Powder | Thin Fakes | Liquid Solution in Ethanol |
| % Non-Volatiles | 100% | 100% | 100% | 100% | 40% |
| Color | Light Yellow | Yellow/Gold | Light Yellow | Amber | Colorless |
| Acid Number (mg KOH/g) | 75 - 89 | 65 - 75 | 75 - 91 | 65 - 75 | - |

FIG. 9

| Sunscreen Number | Manufacturer | Product | Form | SPF |
|---|---|---|---|---|
| 1 | Bayer | Coppertone Kids | Spray | Broad Spectrum SPF 50 |
| 2 | Bayer | Coppertone Water Babies | Lotion | Broad Spectrum SPF 50 |
| 3 | Bayer | Coppertone Sport | Lotion | Broad Spectrum SPF 50 |

FIG. 10

| Sample ID 1006- | Description | Modification | Drawdown Applicator |
|---|---|---|---|
| 301A | 20% Poly-Soleil SY 400 in Ethanol | None | 0.003" |
| 301B | 20% Crystalac Prem. Flake 500 in Ethanol | None | 0.003" |
| 301C | 20% R-49 Refined Bleached Shellac in Ethanol | None | 0.003" |
| 301D | 20% SSB Komet 58 Flake in Ethanol | None | 0.003" |
| Baycusan C 2000 | 40% in Ethanol | | 0.0015" |
| 313A | 20% Poly-Soleil SY 400 in Ethanol | 50% on Solids w/ Baycusan C 2000 | 0.003" |
| 313B | 20% Crystalac Prem. Flake 500 in Ethanol | 50% on Solids w/ Baycusan C 2000 | 0.003" |
| 313C | 20% R-49 Refined Bleached Shellac in Ethanol | 50% on Solids w/ Baycusan C 2000 | 0.003" |
| 313D | 20% SSB Komet 58 Flake in Ethanol | 50% on Solids w/ Baycusan C 2000 | 0.003" |
| 315A | 20% Poly-Soleil SY 400 in Ethanol | 25% on Solids w/ Baycusan C 2000 | 0.003" |
| 315B | 20% Crystalac Prem. Flake 500 in Ethanol | 25% on Solids w/ Baycusan C 2000 | 0.003" |
| 315C | 20% R-49 Refined Bleached Shellac in Ethanol | 25% on Solids w/ Baycusan C 2000 | 0.003" |
| 315D | 20% SSB Komet 58 Flake in Ethanol | 25% on Solids w/ Baycusan C 2000 | 0.003" |

FIG. 11

| Sample ID 1006- | Description | 30-Minute Spots ||| 2-Hour Spots ||| Total Score (Max = 30) |
|---|---|---|---|---|---|---|---|---|
| | | 1 Coppertone Kids Spray SPF 50 | 2 Coppertone Water Babies Lotion SPF 50 | 3 Coppertone Sport SPF 50 | 1 Coppertone Kids Spray SPF 50 | 2 Coppertone Water Babies Lotion SPF 50 | 3 Coppertone Sport SPF 50 | |
| 301A | Poly-Soleil SY 400 | 2.0 | 5.0 | 4.5 | 2.0 | 4.5 | 4.0 | 22.0 |
| 301B | Crystalac Flake 500 | 2.5 | 5.0 | 4.5 | 2.5 | 5.0 | 4.5 | 24.0 |
| 301C | R-49 Refined Bleached | 2.0 | 4.5 | 4.0 | 2.0 | 4.0 | 3.5 | 20.0 |
| 301D | SSB Komet 58 Flake | 2.0 | 5.0 | 4.5 | 1.5 | 5.0 | 4.5 | 22.5 |
| Baycusan C 2000 | Baycusan C 2000 | 1.5 | 1.5 | 1.5 | 2.0 | 1.0 | 1.5 | 9.0 |
| 313A | 50/50 Poly-Soleil SY 400/Bay C 2000 | 2.0 | 4.0 | 3.0 | 2.0 | 4.0 | 2.0 | 17.0 |
| 313B | 50/50 Crystalac Flake 500/Bay C 2000 | 2.0 | 4.0 | 2.0 | 2.0 | 4.0 | 2.0 | 16.0 |
| 313C | 50/50 R-49 Refined Bleached/Bay C 2000 | 2.0 | 4.0 | 2.0 | 2.0 | 1.0 | 1.0 | 12.0 |
| 313D | 50/50 SSB Komet 58 Flake/Bay C 2000 | 2.0 | 4.0 | 2.0 | 2.0 | 4.0 | 2.0 | 16.0 |
| 315A | 75/25 Poly-Soleil SY 400/Bay C 2000 | 2.0 | 5.0 | 4.0 | 2.0 | 4.0 | 3.5 | 20.5 |
| 315B | 75/25 Crystalac Flake 500/Bay C 2000 | 4.0 | 4.5 | 3.0 | 2.0 | 5.0 | 3.0 | 21.5 |
| 315C | 75/25 R-49 Refined Bleached/Bay C 2000 | 2.0 | 4.0 | 3.0 | 2.0 | 3.5 | 2.5 | 17.0 |
| 315D | 75/25 SSB Komet 58 Flake/Bay C 2000 | 2.0 | 5.0 | 3.0 | 2.0 | 5.0 | 2.5 | 19.5 |

FIG. 12

| Product | Poly-Soleil SY 400 | Crystalc Premium Flake 500 | R-49 Refined Bleached Shellac | SSB Komet 58 Flake | Baycusan C 2000 |
|---|---|---|---|---|---|
| Manufacturer | | Mantrose-Hauser Co. | | | Covestro |
| Description | Shellac | Shellac | Shellac | Shellac | Polyurethane |
| Form | Powder | Thin Flakes | Powder | Thin Fakes | Liquid Solution in Ethanol |
| % Non-Volatiles | 100% | 100% | 100% | 100% | 40% |
| Color | Light Yellow | Yellow/Gold | Light Yellow | Amber | Colorless |
| Acid Number (mg KOH/g) | 75 - 89 | 65 - 75 | 75 - 91 | 65 - 75 | - |

FIG. 13

| Sunscreen Number | Manufacturer | Product | Form | Broad Spectrum SPF |
|---|---|---|---|---|
| 1 | Bayer | Coppertone Kids | Spray | 50 |
| 2 | Bayer | Coppertone Water Babies | Lotion | 50 |
| 3 | Bayer | Coppertone Sport | Lotion | 50 |
| 4 | Bayer | Coppertone Sport | Lotion | 15 |
| 5 | Bayer | Coppertone Tanning | Lotion | 8 |

FIG. 14

| Sample ID 1006- | Ink Polymer (in Ethanol) |
|---|---|
| 317A | Poly-Soleil SY 400 |
| 317B | Crystalac Flake 500 |
| 317C | R-49 Refined Bleached |
| 317D | SSB Komet 58 Flake |
| 317E | 75/25 Poly-Soleil SY 400/Bay C 2000 |
| 317F | 75/25 Crystalac Flake 500/Bay C 2000 |
| 317G | 75/25 R-49 Refined Bleached/Bay C 2000 |
| 317H | 75/25 SSB Komet 58 Flake/Bay C 2000 |

FIG. 15

| Test Reagent Spot No. | Description | Type | 317A - Time of Sun Exposure | | | | | | After Wash Color & Other |
|---|---|---|---|---|---|---|---|---|---|
| | | | Initial | 30 Minutes | 1 Hour | 2 Hours | 3 Hours | 4 Hours | |
| | Color of Control Area (No Sunscreen) | | Blue | Pink | Pink/Orange | Light Orange | Light Orange | Orange | Orange |
| 1 | Coppertone Kids Broad Spectrum SPF 50 | Spray | 5 | 5 | 5 | 5 | 5 | NR | 4-5 |
| 2 | Coppertone Water Babies SPF 50 | Lotion | 4 | 4 | 4 | 4 | 4 | NR | 3-4 |
| 3 | Coppertone Sport SPF50 | Lotion | 4-5 | 4-5 | 4-5 | 4-5 | 5 | NR | 3 |
| 4 | Coppertone Sport SPF15 | Lotion | 4 | 4 | 4 | 4 | 5 | NR | 3-4 |
| 5 | Coppertone Tanning SPF8 | Lotion | 2 | 2 | 2 | 2 | 2 | NR | 3-4 |
| Irradiance Level of Sun (MED/Hr) | | | 1.6 | 1.9 - 2.0 | 1.8 | 2.2 | 1.4 - 1.8 | 1.7 | 1.2 - 1.3 |

FIG. 16

| Test Reagent Spot No. | Description | Type | 317B - Time of Sun Exposure | | | | | | After Wash Color & Other |
|---|---|---|---|---|---|---|---|---|---|
| | | | Initial | 30 Minutes | 1 Hour | 2 Hours | 3 Hours | 4 Hours | |
| | Color of Control Area (No Sunscreen) | | Bright Blue | Bright Blue | Bright Blue | Bright Blue | Bright Blue | Bright Blue | Bright Blue |
| 1 | Coppertone Kids Broad Spectrum SPF 50 | Spray | 5 | 5 | 4-5 | 4-5 | 4-5 | 4-5 | 4-5 |
| 2 | Coppertone Water Babies SPF 50 | Lotion | 3 | 3 | 3 | 3 | 3 | 1-3 | 1 |
| 3 | Coppertone Sport SPF50 | Lotion | 4 | 4 | 4 | 4 | 4 | 4 | 1 |
| 4 | Coppertone Sport SPF15 | Lotion | 3-4 | 3-4 | 3-4 | 3-4 | 3-4 | 3 | 1 |
| 5 | Coppertone Tanning SPF8 | Lotion | 2 | 2 | 2 | 1-2 | 1-2 | 1-2 | 1 |
| Irradiance Level of Sun (MED/Hr) | | | 1.6 - 1.7 | 1.9 - 2.0 | 1.8 - 1.9 | 2.2 | 1.4 - 1.8 | 1.7 | 1.2 - 1.3 |

FIG. 17

| Test Reagent Spot No. | Description | Type | 317C - Time of Sun Exposure | | | | | | After Wash Color & Other |
|---|---|---|---|---|---|---|---|---|---|
| | | | Initial | 30 Minutes | 1 Hour | 2 Hours | 3 Hours | 4 Hours | |
| | Color of Control Area (No Sunscreen) | | Slight Grey Blue | Slight Grey Blue | Grey Blue | Orange & Blue | Orange & Blue | Orange & Blue | Orange & Blue |
| 1 | Coppertone Kids Broad Spectrum SPF 50 | Spray | 5 | 4-5 | 4-5 | 4 | 4 | 4 | 4-5 |
| 2 | Coppertone Water Babies SPF 50 | Lotion | 3 | 3 | 3 | 3 | 3 | 3 | 1-2 |
| 3 | Coppertone Sport SPF50 | Lotion | 4 | 4-5 | 4-5 | 4 | 4 | 4 | 1 |
| 4 | Coppertone Sport SPF15 | Lotion | 3 | 3-4 | 3-4 | 3-4 | 3-4 | 3-4 | 1-2 |
| 5 | Coppertone Tanning SPF8 | Lotion | 2 | 2 | 2 | 1 | 1 | 1 | 2 |
| Irradiance Level of Sun (MED/Hr) | | | 1.6 - 1.7 | 1.9 | 1.9 | 2.3 - 2.4 | 1.2 - 1.3 | 1.2 - 1.3 | 1.3 |

FIG. 18

| Test Reagent Spot No. | Description | Type | 317D - Time of Sun Exposure ||||||| After Wash Color & Other |
|---|---|---|---|---|---|---|---|---|---|
| | | | Initial | 30 Minutes | 1 Hour | 2 Hours | 3 Hours | 4 Hours | |
| Color of Control Area (No Sunscreen) | | | Bright Blue | Bright Blue | Bright Blue | Bright Blue | Blue | Blue | Blue |
| 1 | Coppertone Kids Broad Spectrum SPF 50 | Spray | 5 | 5 | 5 | 5 | 4-5 | 4-5 | 4-5 |
| 2 | Coppertone Water Babies SPF 50 | Lotion | 3 | 3 | 3 | 3 | 3 | 3 | 1 |
| 3 | Coppertone Sport SPF50 | Lotion | 4 | 3-4 | 3-4 | 3-4 | 3-4 | 3-4 | 1 |
| 4 | Coppertone Sport SPF15 | Lotion | 4 | 3-4 | 3-4 | 3-4 | 3-4 | 3-4 | 1 |
| 5 | Coppertone Tanning SPF8 | Lotion | 2 | 2 | 1-2 | 1-2 | 1-2 | 1-2 | 1 |
| Irradiance Level of Sun (MED/Hr) | | | 1.6 - 1.7 | 1.9 | 1.9 | 2.3 - 2.4 | 1.2 - 1.4 | 1.2 - 1.3 | 1.3 |

FIG. 19

| Test Reagent Spot No. | Description | Type | 317E - Time of Sun Exposure ||||||| After Wash Color & Other |
| --- | --- | --- | --- | --- | --- | --- | --- | --- | --- |
| | | | Initial | 30 Minutes | 1 Hour | 2 Hours | 3 Hours | 4 Hours | |
| | Color of Control Area (No Sunscreen) | | Grey Blue | Yellow Blue | Dark Yellow | Orange | Orange | Orange | Orange |
| 1 | Coppertone Kids Broad Spectrum SPF 50 | Spray | 5 | 5 | 5 | 4-5 | NR | NR | 4-5 |
| 2 | Coppertone Water Babies SPF 50 | Lotion | 3-4 | 3-4 | 3-4 | 3-4 | NR | NR | 4-5 |
| 3 | Coppertone Sport SPF50 | Lotion | 5 | 5 | 5 | 5 | NR | NR | 4-5 |
| 4 | Coppertone Sport SPF15 | Lotion | 4 | 4 | 4 | 4-5 | NR | NR | 4-5 |
| 5 | Coppertone Tanning SPF8 | Lotion | 2 | 2 | 2 | 3 | NR | NR | 5 |
| Irradiance Level of Sun (MED/Hr) | | | 1.8 | 1.8 - 1.9 | 2.1 | 1.7 | 1.6 - 1.7 | 1.3 | 1.3 |

FIG. 20

| Test Reagent Spot No. | Description | Type | 317F - Time of Sun Exposure | | | | | | After Wash Color & Other |
|---|---|---|---|---|---|---|---|---|---|
| | | | Initial | 30 Minutes | 1 Hour | 2 Hours | 3 Hours | 4 Hours | |
| | Color of Control Area (No Sunscreen) | | Bright Blue | Bright Blue | Bright Blue | Blue | Blue | Blue | Blue |
| 1 | Coppertone Kids Broad Spectrum SPF 50 | Spray | 5 | 4-5 | 4-5 | 4-5 | 4-5 | 4-5 | 5 |
| 2 | Coppertone Water Babies SPF 50 | Lotion | 3 | 3 | 3 | 3 | 3 | 3 | 3 |
| 3 | Coppertone Sport SPF50 | Lotion | 4 | 4 | 4 | 4 | 4 | 4 | 4 |
| 4 | Coppertone Sport SPF15 | Lotion | 4 | 3-4 | 3-4 | 3-4 | 3-4 | 3-4 | 3-4 |
| 5 | Coppertone Tanning SPF8 | Lotion | 2 | 1-2 | 1-2 | 1-2 | 1-2 | 1-2 | 3 |
| Irradiance Level of Sun (MED/Hr) | | | 1.8 | 1.8 - 1.9 | 2.1 | 1.7 | 1.6 - 1.7 | 1.3 | 1.3 |

FIG. 21

| Test Reagent Spot No. | Description | Type | 317G - Time of Sun Exposure ||||||  After Wash Color & Other |
|---|---|---|---|---|---|---|---|---|---|
| | | | Initial | 30 Minutes | 1 Hour | 2 Hours | 3 Hours | 4 Hours | |
| | Color of Control Area (No Sunscreen) | | Bright Blue | Bright Blue | Blue | Orange | Orange | Orange | Orange |
| 1 | Coppertone Kids Broad Spectrum SPF 50 | Spray | 5 | 5 | 5 | 5 | NR | NR | 4-5 |
| 2 | Coppertone Water Babies SPF 50 | Lotion | 3 | 3 | 3 | 3 | NR | NR | 3 |
| 3 | Coppertone Sport SPF50 | Lotion | 4 | 4 | 4 | 4 | NR | NR | 4-4 |
| 4 | Coppertone Sport SPF15 | Lotion | 3-4 | 3-4 | 3-4 | 3 | NR | NR | 3-4 |
| 5 | Coppertone Tanning SPF8 | Lotion | 2 | 2 | 1-2 | 1-2 | NR | NR | 3 |
| Irradiance Level of Sun (MED/Hr) | | | 1.9 | 1.9 | 2.0 | 1.7 | 1.4 | 1.3 | 1.1 - 1.3 |

FIG. 22

| Test Reagent Spot No. | Description | Type | 317H - Time of Sun Exposure ||||||| After Wash Color & Other |
| --- | --- | --- | --- | --- | --- | --- | --- | --- | --- |
| | | | Initial | 30 Minutes | 1 Hour | 2 Hours | 3 Hours | 4 Hours | |
| | Color of Control Area (No Sunscreen) | | Blue | Blue | Blue | Blue | Blue | Blue | Blue |
| 1 | Coppertone Kids Broad Spectrum SPF 50 | Spray | 5 | 4-5 | 4-5 | 4-5 | 4-5 | 4-5 | 5 |
| 2 | Coppertone Water Babies SPF 50 | Lotion | 3 | 3 | 3 | 3 | 3 | 3 | 2-3 |
| 3 | Coppertone Sport SPF50 | Lotion | 4 | 4 | 4 | 4 | 4 | 4 | 4 |
| 4 | Coppertone Sport SPF15 | Lotion | 3-4 | 3-4 | 3-4 | 3-4 | 3-4 | 3 | 3-4 |
| 5 | Coppertone Tanning SPF8 | Lotion | 2 | 1-2 | 1-2 | 1-2 | 1-2 | 1-2 | 1-2 |
| Irradiance Level of Sun (MED/Hr) | | | 1.9 | 1.9 | 2.0 | 1.7 | 1.4 | 1.3 | 1.1 - 1.3 |

FIG. 23

| Product | Crystalc Premium Flake 500 | SSB Komet 58 Flake |
|---|---|---|
| Manufacturer | Mantrose-Hauser Co. | |
| Description | Shellac | Shellac |
| Form | Thin Flakes | Thin Fakes |
| % Non-Volatiles | 100% | 100% |
| Color | Yellow/Gold | Amber |
| Acid Number (mg KOH/g) | 65 - 75 | 65 - 75 |

FIG. 24

| Sunscreen Number | Manufacturer | Product | Form | Broad Spectrum SPF |
|---|---|---|---|---|
| 1 | Bayer | Coppertone Water Babies | Lotion | 50 |
| 2 | Bayer | Coppertone Sport | Lotion | 50 |
| 3 | Bayer | Coppertone Sport | Lotion | 15 |
| 4 | Bayer | Coppertone Tanning | Lotion | 8 |

FIG. 25

| Sample ID 1006- | Ink Polymer (in Ethanol) |
|---|---|
| 317B | Crystalac Flake 500 |
| 319A | Crystalac Flake 500 |
| 319B | Crystalac Flake 500 |
| 319C | Crystalac Flake 500 |
| 319D | Crystalac Flake 500 |
| 317D | SSB Komet 58 Flake |
| 319E | SSB Komet 58 Flake |
| 319F | SSB Komet 58 Flake |
| 319G | SSB Komet 58 Flake |
| 319H | SSB Komet 58 Flake |

FIG. 26

| Ink ID 1006- | Ink Polymer (in Ethanol) | Dye (% on TBS) | Initial Color (Not Activated) | Activated Color | Unprotected Area Fade After 4 Hours Sunlight | Effectiveness of Sunscreens | Color After 4 Hours Sunlight & Sunscreen Removal vs Unprotected Area |
|---|---|---|---|---|---|---|---|
| 317B | Crystalac Flake 500 | 1% Oxford Blue | Colorless | Blue | Slight Fade | Good | Darker |
| 319A | Crystalac Flake 500 | 1% Palatinate Purple | Teal Green | Vibrant Blue | Severe Fade | Not Good | Darker |
| 319B | Crystalac Flake 500 | 0.5% Plum Red | Pale Blue Purple | Vibrant Blue | Severe Fade | Good | Darker |
| 319C | Crystalac Flake 500 | 1% Rush Yellow | Colorless | Orange | Slight Fade | Good | Darker |
| 319D | Crystalac Flake 500 | 1% Gold | Colorless | Orange | Moderate Fade | Moderate | Same |
| 317D | SSB Komet 58 Flake | 1% Oxford Blue | Slight Yellow | Blue | Slight Fade | Good | Darker |
| 319E | SSB Komet 58 Flake | 1% Palatinate Purple | Yellow Green | Vibrant Blue | Severe Fade | Not Good | Darker |
| 319F | SSB Komet 58 Flake | 0.5% Plum Red | Pale Blue | Dark Blue | Severe Fade | Good | Same |
| 319G | SSB Komet 58 Flake | 1% Rush Yellow | Slight Yellow | Orange | Slight Fade | Good | Darker |
| 319H | SSB Komet 58 Flake | 1% Gold | Slight Yellow | Reddish Orange | Slight Fade | Moderate | Same |

FIG. 27

| Test Reagent Spot No. | Description | Type | 317B - Time of Sun Exposure ||||  After Wash Color & Other |
|---|---|---|---|---|---|---|
| | | | Initial | 1 Hour | 4 Hours | |
| | Color of Control Area (No Sunscreen) | | Blue | Blue | Light Blue | Light Blue |
| 1 | Coppertone Water Babies SPF 50 | Lotion | 3 | 3 | 3 | 1 |
| 2 | Coppertone Sport SPF50 | Lotion | 4 | 4 | 4 | 1 Darker |
| 3 | Coppertone Sport SPF15 | Lotion | 3 | 3 | 3 | 1 Darker |
| 4 | Coppertone Tanning SPF8 | Lotion | 2 | 2 | 1-2 | 1 |
| Irradiance Level of Sun (MED/Hr) | | | 1.9 | 1.9 | 0.7 | 0.4 |

FIG. 28

| Test Reagent Spot No. | Description | Type | 319A - Time of Sun Exposure ||||After Wash Color & Other |
| --- | --- | --- | --- | --- | --- | --- |
| | | | Initial | 1 Hour | 4 Hours | |
| | Color of Control Area (No Sunscreen) | | Bright Teal Blue | Bright Blue | Bright/Light Blue | Bright/Light Blue |
| 1 | Coppertone Water Babies SPF 50 | Lotion | 1-2 | 1-2 | 1-2 | 1-2 Darker |
| 2 | Coppertone Sport SPF50 | Lotion | 1-2 | 1-2 | 1 | 1 Darker |
| 3 | Coppertone Sport SPF15 | Lotion | 1-2 | 1-2 | 1 | 1 Darker |
| 4 | Coppertone Tanning SPF8 | Lotion | 1 | 1 | 1 | 1-2 Darker |
| Irradiance Level of Sun (MED/Hr) | | | 1.7 | 2.0 | 1.1 | 0.9 |

| Test Reagent Spot No. | Description | Type | 319B - Time of Sun Exposure | | | | After Wash Color & Other |
|---|---|---|---|---|---|---|---|
| | | | Initial | 1 Hour | 4 Hours | | |
| | Color of Control Area (No Sunscreen) | | Blue | Blue | Light Blue | | Light Blue |
| 1 | Coppertone Water Babies SPF 50 | Lotion | 2 | 2 | 1-2 | | 2 |
| 2 | Coppertone Sport SPF50 | Lotion | 3 | 3 | 2 | | 1 Darker |
| 3 | Coppertone Sport SPF15 | Lotion | 2-3 | 2-3 | 1-2 | | 1-2 Darker |
| 4 | Coppertone Tanning SPF8 | Lotion | 1-2 | 1 | 1 | | 2 |
| Irradiance Level of Sun (MED/Hr) | | | 1.7 | 2.0 | 1.1 | | 0.8 |

| Test Reagent Spot No. | Description | Type | 319C - Time of Sun Exposure | | | | After Wash Color & Other |
|---|---|---|---|---|---|---|---|
| | | | Initial | 1 Hour | 4 Hours | | |
| | Color of Control Area (No Sunscreen) | | Orange | Orange | Orange | | Orange |
| 1 | Coppertone Water Babies SPF 50 | Lotion | 3 | 3 | 3 | | 1 Darker |
| 2 | Coppertone Sport SPF50 | Lotion | 4 | 4 | 4 | | 1-2 Darker |
| 3 | Coppertone Sport SPF15 | Lotion | 3 | 3 | 3 | | 1 Darker |
| 4 | Coppertone Tanning SPF8 | Lotion | 2 | 2 | 1-2 | | 1-2 Darker |
| | Irradiance Level of Sun (MED/Hr) | | 1.7 | 2.0 | 1.0 | | 0.7 |

FIG. 31

| Test Reagent Spot No. | Description | Type | 319D - Time of Sun Exposure ||| After Wash Color & Other |
| --- | --- | --- | --- | --- | --- | --- |
| | | | Initial | 1 Hour | 4 Hours | |
| | Color of Control Area (No Sunscreen) | | Reddish Orange | Reddish Orange | Light Reddish Orange | Light Reddish Orange |
| 1 | Coppertone Water Babies SPF 50 | Lotion | 2 | 2 | 1-2 | 1-2 |
| 2 | Coppertone Sport SPF50 | Lotion | 3 | 3 | 2-3 | 1 |
| 3 | Coppertone Sport SPF15 | Lotion | 2 | 2 | 2 | 1 |
| 4 | Coppertone Tanning SPF8 | Lotion | 1 | 1 | 1 | 1-2 |
| Irradiance Level of Sun (MED/Hr) | | | 1.7 | 2.0 | 1.0 | 0.7 |

FIG. 32

| Test Reagent Spot No. | Description | Type | 317D - Time of Sun Exposure ||| After Wash Color & Other |
| --- | --- | --- | --- | --- | --- | --- |
| | | | Initial | 1 Hour | 4 Hours | |
| | Color of Control Area (No Sunscreen) | | Blue | Blue | Light Blue | Light Blue |
| 1 | Coppertone Water Babies SPF 50 | Lotion | 3 | 3 | 3 | 1 Darker |
| 2 | Coppertone Sport SPF50 | Lotion | 4 | 4 | 4 | 1 Darker |
| 3 | Coppertone Sport SPF15 | Lotion | 3-4 | 3-4 | 2-3 | 1 |
| 4 | Coppertone Tanning SPF8 | Lotion | 2 | 2 | 1-2 | 1 |
| | Irradiance Level of Sun (MED/Hr) | | 2.0 | 1.9 | 0.7 | 0.4 |

FIG. 33

| Test Reagent Spot No. | Description | Type | 319E - Time of Sun Exposure ||||  After Wash Color & Other |
| --- | --- | --- | --- | --- | --- | --- |
| | | | Initial | 1 Hour | 4 Hours | |
| Color of Control Area (No Sunscreen) | | | Bright Teal Blue | Bright Blue | Bright/ Light Blue | Bright/ Light Blue |
| 1 | Coppertone Water Babies SPF 50 | Lotion | 1-2 | 1-2 | 1-2 | 2 Darker |
| 2 | Coppertone Sport SPF50 | Lotion | 1-2 | 1-2 | 1 | 1 Darker |
| 3 | Coppertone Sport SPF15 | Lotion | 1-2 | 1-2 | 1 | 1-2 Darker |
| 4 | Coppertone Tanning SPF8 | Lotion | 1 | 1 | 1 | 2 Darker |
| Irradiance Level of Sun (MED/Hr) | | | 1.8 | 2.0 | 0.8 | 0.7 |

FIG. 34

| Test Reagent Spot No. | Description | Type | 319F - Time of Sun Exposure ||| After Wash Color & Other |
| --- | --- | --- | --- | --- | --- | --- |
| | | | Initial | 1 Hour | 4 Hours | |
| | Color of Control Area (No Sunscreen) | | Blue | Blue | Light Blue | Light Blue |
| 1 | Coppertone Water Babies SPF 50 | Lotion | 2 | 2 | 1-2 | 1-2 |
| 2 | Coppertone Sport SPF50 | Lotion | 3 | 3 | 2-3 | 1-2 |
| 3 | Coppertone Sport SPF15 | Lotion | 2-3 | 2-3 | 2 | 1-2 |
| 4 | Coppertone Tanning SPF8 | Lotion | 1-2 | 1-2 | 1-2 | 1 |
| Irradiance Level of Sun (MED/Hr) | | | 1.9 | 1.9 | 0.8 | 0.7 |

FIG. 35

| Test Reagent Spot No. | Description | Type | 319G - Time of Sun Exposure ||| After Wash Color & Other |
| | | | Initial | 1 Hour | 4 Hours | |
|---|---|---|---|---|---|---|
| | Color of Control Area (No Sunscreen) | | Orange | Orange | Light Orange | Light Orange |
| 1 | Coppertone Water Babies SPF 50 | Lotion | 3 | 3 | 3 | 1 Darker |
| 2 | Coppertone Sport SPF50 | Lotion | 4 | 4 | 4 | 1 Darker |
| 3 | Coppertone Sport SPF15 | Lotion | 3 | 3 | 2-3 | 1 Darker |
| 4 | Coppertone Tanning SPF8 | Lotion | 2 | 2 | 1-2 | 1 Darker |
| Irradiance Level of Sun (MED/Hr) | | | 1.9 | 2.0 | 0.7 | 0.4 |

FIG. 36

| Test Reagent Spot No. | Description | Type | 319H - Time of Sun Exposure | | | After Wash |
|---|---|---|---|---|---|---|
| | | | Initial | 1 Hour | 4 Hours | Color & Other |
| | Color of Control Area (No Sunscreen) | | Reddish Orange | Reddish Orange | Lighter Reddish Orange | Lighter Reddish Orange |
| 1 | Coppertone Water Babies SPF 50 | Lotion | 2 | 2 | 2 | 1 |
| 2 | Coppertone Sport SPF50 | Lotion | 3 | 3 | 3 | 1 |
| 3 | Coppertone Sport SPF15 | Lotion | 2 | 2 | 1-2 | 1-2 |
| 4 | Coppertone Tanning SPF8 | Lotion | 1 | 1 | 1 | 1 |
| Irradiance Level of Sun (MED/Hr) | | | 1.9 | 2.0 | 0.7 | 0.4 |

FIG. 37

| Test Reagent Spot No. | Description | Type | 319C - Time of Sun Exposure ||| After Dry Wipe with Terry Towel | After Wash Color & Other |
|---|---|---|---|---|---|---|---|
| | | | Initial | 1 Hour | 4 Hours | | |
| | Color of Control Area (No Sunscreen) | | Orange | Orange | Orange | Orange | Orange |
| | Foil Area | | | | | Same | Slightly Darker |
| A | Coppertone Water Babies SPF 50 | Lotion | 4-5 | 4-5 | 4-5 | 4-5 | 1 |
| B | Coppertone Sport SPF50 | Lotion | 5 | 5 | 5 | 4-5 | 1-2 |
| C | Coppertone Sport SPF15 | Lotion | 5 | 5 | 5 | 4-5 | 1-2 |
| D | Coppertone Tanning SPF8 | Lotion | 5 | 5 | 5 | 4-5 | 2 |
| | Irradiance Level of Sun (MED/Hr) | | 2.8 | 1.2 - 2.8 | 0.6 - 0.8 | 0.6 - 0.8 | 1.1 - 1.2 |

FIG. 38

| Sunscreen Spot | Approximate Volume of Sport 50 (uL) | Coverage (uL/cm²) | Sunblocking After 4 Hours | Removal of Sunscreen After Dry Wipe | Removal of Sunscreen After Wash |
|---|---|---|---|---|---|
| A | 10 | 0.56 | Good | Very Little | All Removed |
| B | 20 | 1.11 | Excellent | Very Little | Nearly All Removed |
| C | 40 | 2.22 | Excellent | Very Little | Nearly All Removed |
| D | 80 | 4.44 | Excellent | Very Little | Nearly All Removed |

FIG. 39

| Sunscreen Number | Manufacturer | Product | Form | Broad Spectrum SPF |
|---|---|---|---|---|
| 1 | Bayer | Coppertone Water Babies | Lotion | 50 |
| 2 | Bayer | Coppertone Sport | Lotion | 50 |
| 3 | Bayer | Coppertone Sport | Lotion | 15 |
| 4 | Bayer | Coppertone Tanning | Lotion | 8 |

FIG. 40

| Yellow Ink ID | Description (Mods @ % of Total Formulation) | Compatibility | Appearance of Drawdowns on PVC Charts |
|---|---|---|---|
| 350A | Control 331C - Yellow Ink (No Mods) | - | Good |
| 350B | Dow FC 5002 ID Resin Gum @ 2% | Severe settling, no mixable | Not testable |
| 350C | Dow FA 4003 DM @ 2% | Good | Dewetted |
| 350D | ShinEtsu KP-545 @ 2% | Severe settling, no mixable | Not testable |
| 350E | AE Silk Clay V @ 5% | Soft settle, mixable | Gritty, ok |
| 350F | Tego Glide 440 @ 1% | Good | Good |
| 350G | Dow 556 Fluid @ 2% | Good | Good |
| 350H | Silsense CP1 @ 2% | Not soluble, poor | Not testable |
| 350J | Silube J208-612 @ 2% | Settling, mixable | Good |
| 350K | Silube J208-812 @ 2% | Settling, mixable | Good |
| 350L | Silsurf A208 @ 2% | Settling, mixable | Good |
| 350M | Silwax D0-MS @ 2% | Good | Good |
| 350N | Silube J208-612 & 812 each @ 2% | Good | Good |

FIG. 41

| Yellow Ink ID | Description (Mods @ % of Total Formulation) | Sunscreen Removal Results | | | | | | | | | | | | Total Score (Max = 60) |
|---|---|---|---|---|---|---|---|---|---|---|---|---|---|---|
| | | 300g Wipe | | | | 1000g Wipe | | | | 80 Min Water Immersion | | | | |
| | | Dry | | Wet | | Dry | | Wet | | Distilled Water | | Tap Water | | |
| | | WB | Sport | WB | Sport | WB | Sport | WB | Sport | WB | Sport | WB | Sport | |
| 350A | Control 331C - Yellow Ink (No Mods) | 2.5 | 2.0 | 4.0 | 2.5 | 4.0 | 2.5 | 5.0 | 3.5 | 2.0 | 1.0 | 2.0 | 1.0 | 32.0 |
| 350E | AE Silk Clay V @ 5% | 2.5 | 2.0 | 2.5 | 2.0 | 3.5 | 2.5 | 3.5 | 2.5 | 1.0 | 1.0 | 1.0 | 1.0 | 25.0 |
| 350F | Tego Glide 440 @ 1% | 3.0 | 2.5 | 4.5 | 3.0 | 4.5 | 3.0 | 5.0 | 3.5 | 1.2 | 1.0 | 2.5 | 1.0 | 34.7 |
| 350G | Dow 556 Fluid @ 2% | 3.0 | 2.0 | 4.0 | 3.5 | 4.0 | 3.5 | 5.0 | 3.5 | 2.0 | 1.0 | 2.5 | 1.0 | 35.0 |
| 350J | Silube J208-612 @ 2% | 3.5 | 2.0 | 4.0 | 3.5 | 4.0 | 2.5 | 5.0 | 4.0 | 2.0 | 1.0 | 2.0 | 1.0 | 34.5 |
| 350K | Silube J208-812 @ 2% | 3.0 | 2.0 | 4.0 | 4.0 | 4.0 | 2.5 | 5.0 | 4.0 | 2.0 | 1.0 | 2.0 | 1.0 | 34.5 |
| 350L | Silsurf A208 @ 2% | 3.0 | 2.5 | 4.0 | 3.5 | 4.5 | 3.5 | 5.0 | 4.5 | 2.0 | 1.0 | 2.0 | 1.0 | 36.5 |
| 350M | Silwax DO-MS @ 2% | 3.0 | 2.0 | 4.0 | 3.5 | 3.0 | 2.5 | 5.0 | 4.0 | 2.0 | 1.0 | 2.0 | 1.0 | 33.0 |
| 350N | Silube J208-612 & 812 each @ 2% | 3.0 | 2.0 | 4.0 | 3.0 | 4.5 | 2.5 | 5.0 | 3.0 | 2.0 | 1.0 | 2.0 | 1.0 | 33.0 |

FIG. 42

| Yellow Ink ID | Description | Compatibility | Appearance of Drawdowns on PVC Charts |
|---|---|---|---|
| 355A | 331A Yellow Control | Good | Good |
| 355B | 2% Dow FA 4004 | Slight Immiscibility | Slight Dewetting |
| 355C | 2% Silsurf Di-1010 | Good | Good |
| 355D | 2% SPI 5815 | Slight Immiscibility | Dewetting |
| 355E | 2% SPI 5816 | Settling | Dewetting |
| 355F | 2% Belsil PDM 1000 | Good | Good; Slightly Gritty |

FIG. 43

| Yellow Ink ID | Description | Sunscreen Removal Results | | Total Score (Max = 10) |
| --- | --- | --- | --- | --- |
| | | 300g Dry Wipe | | |
| | | WB | Sport | |
| 355A | 331A Yellow Control | 3.0 | 3.0 | 6.0 |
| 355B | 2% Dow FA 4004 | 3.5 | 3.0 | 6.5 |
| 355C | 2% Silsurf Di-1010 | 3.5 | 3.0 | 6.5 |
| 355D | 2% SPI 5815 | 3.5 | 3.0 | 6.5 |
| 355E | 2% SPI 5816 | 3.5 | 3.0 | 6.5 |
| 355F | 2% Belsil PDM 1000 | 4.0 | 3.0 | 7.0 |

FIG. 44

| Ink ID | Description | Liquid Ink Compatibility | Appearance of Drawdowns on PVC Charts | Inks on Rubber Sheets | | Sunscreen Removal Results | | Total Score (Max = 15) |
|---|---|---|---|---|---|---|---|---|
| | | | | Appearance | "SNAP" Test (90° Bend & Rub Test) | 300g Dry Wipe | | |
| | | | | | | WB | Sport | |
| 366A | 331B Control Yellow Ink | Slight settling | Good | Good | 1.0 | 5.0 | 3.5 | 9.5 |
| 366B | 25% NatureFlexx 509 | Good | Good | Severe Dewetting | 2.0 | 3.5 | 3.0 | 8.5 |
| 366C | 25% SynPlicity 1000 | Good | Good- Slightly gritty | Severe Dewetting | 4.5 | 4.0 | 2.0 | 10.5 |
| 366D | 25% Carbowax Sentry PEG 400 | Good | Very sticky- bad | Untestable | 1.0 | 1.0 | 1.0 | 3.0 |
| 366E | 25% PEG 400 DL | Good | Good | Severe Dewetting | 2.5 | 4.0 | 3.0 | 9.5 |
| 366F | 25% Pelemol DIA | Good | Good | Severe Dewetting | 4.5 | 4.0 | 3.0 | 11.5 |
| 366G | 25% Octyl Isonanoate | Good | Severe Dewetting | Severe Dewetting | 1.5 | x | x | 1.5 |
| 366H | 25% Purolan ATBC-C | Good | Good- Peels easy | Slight Dewetting | 1.5 | 3.0 | 2.0 | 6.5 |
| 366J | 25% Xiameter OFX-5220 | Good | Good | Good | 1.0 | 3.0 | 2.5 | 6.5 |
| 367A | 359A Control Blue Ink | Good | Good | Slight Dewetting | 1.0 | 5.0 | 3.0 | 9.0 |
| 367B | 25% NatureFlexx 509 | Good | Dewetting | Severe Dewetting | 1.0 | x | x | 1.0 |
| 367C | 25% SynPlicity 1000 | Good | Good- Slightly gritty | Severe Deweeting | 4.5 | 5.0 | 3.0 | 12.5 |
| 367D | 25% Carbowax Sentry PEG 400 | Good | Very sticky- bad | Severe Dewetting | 1.0 | x | x | 1.0 |
| 367E | 25% PEG 400 DL | Good | Good- Slimy | Severe Dewetting | 1.0 | 5.0 | 3.0 | 9.0 |
| 367F | 25% Pelemol DIA | Good | Good | Severe Dewetting | 1.0 | 4.5 | 1.5 | 7.0 |
| 367G | 25% Octyl Isonanoate | Good | Severe Dewetting | Severe Dewetting | 1.0 | x | x | 1.0 |
| 367H | 25% Purolan ATBC-C | Good | Dewetting | Severe Dewetting | 1.0 | 5.0 | 1.5 | 7.5 |
| 367J | 25% Xiameter OFX-5220 | Good | Perfect | Good | 1.0 | 4.0 | 3.0 | 8.0 |

FIG. 45 A

Preferred Embodiment: 2/19/2016

| Component | Purpose | Ink Formulation | Approximate Percentages * |
|---|---|---|---|
| Polymer matrix | Support matrix for colorant, film former | Natural biopolymer (Shellac) | ~20-35% |
| Photochromic Colorant(s) | Initial color change with UV light activation | One or More Oxazines | < 1% - 3% |
| Solvents | Diluent, Liquid support medium for mixing, balanced for performance and processing | SD Alcohol 40 (Denatured Alcohol) | ~55-80% |

More Preferred Embodiment: Ink 319C - Yellow Ink 5/5/2017

| Component | Purpose | Ink Formulation | Approximate Percentages * |
|---|---|---|---|
| Polymer matrix | Support matrix for colorant, film former | Natural biopolymer (Shellac) | 15-20% |
| Photochromic Colorant(s) | Initial color change with UV light activation | One or More Oxazines & Pyrans | 0.1-2.0% |
| Solvents | Diluent, Liquid support medium for mixing, balanced for performance and processing | Denatured Alcohol | 70-85% |
| | | Ethyl Acetate | 5-10% |

FIG. 45 B

Most Preferred Embodiment: Ink 330C - Yellow Ink  6/7/2017

| Component | Purpose | Ink Formulation | Approximate Percentages * |
|---|---|---|---|
| Polymer matrix | Support matrix for colorant, film former | Natural biopolymer (Shellac) | 20-30% |
| Photochromic Colorant(s) | Initial color change with UV light activation | One or More Oxazines & Pyrans | 0.1-2.0% |
| Solvents | Diluent, Liquid support medium for mixing, balanced for performance and processing | Denatured Alcohol | 35-45% |
| | | Ethyl Acetate | 20-35% |

Most Preferred Embodiment: Ink 358E - Yellow Ink  11/22/2017

| Component | Purpose | Ink Formulation | Approximate Percentages * |
|---|---|---|---|
| Polymer matrix | Support matrix for colorant, film former | Natural biopolymer (Shellac) | 20-30% |
| Photochromic Colorant(s) | Initial color change with UV light activation | One or More Oxazines & Pyrans | 0.1-2.0% |
| Solvents | Diluent, Liquid support medium for mixing, balanced for performance and processing | Denatured Alcohol | 35-40% |
| | | Ethyl Acetate | 15-25% |
| Plasticizer | Increase flexibility of ink on skin | Soy Ester | 10-20% |

PHOTOCHROMIC COMPOSITIONS, MARKERS CONTAINING THE SAME, AND SYSTEMS AND METHODS FOR THEIR USE

CROSS REFERENCE TO RELATED APPLICATIONS

The present application is a continuation-in-part of PCT/US2017/047751 filed 21 Aug. 2017, which claims priority from U.S. provisional application 62/377,033 filed 19 Aug. 2016. The contents of the PCT application and the provisional application are incorporated herein by reference in their entirety.

FIELD OF THE INVENTION

The present invention pertains generally to photochromic compositions and markers, and to skin care products, such as lotions, sunscreens, sunblocks, and other skin-protection products and cosmetics, that may be used with the compositions and markers. More particularly, the present invention pertains to a photochromic composition and marker and to a system comprising the composition, marker and a sunscreen product that are designed to increase wearing of sunscreen, or alternatively as a reminder to re-apply sunscreen. It is recognized that the system and compositions disclosed may also be used in other skin care products and cosmetics.

DESCRIPTION OF THE RELATED ART

A variety of cosmetic, personal care, consumer and medicinal products, including over-the-counter and pharmaceutical products, could benefit by using visual calorimetric signals responsive to changes in light. For example, there is growing recognition of the fact that over-exposure to the sun's rays is instrumental in causing aging of the skin and the development of related medical conditions such as skin cancer. A variety of sun care products have been developed to help reduce the risks associated with exposure to the sun. For example, some products use color as an indicator to determine whether the product has been initially applied over the desired skin areas. Some such products go on colored and become invisible as they are rubbed into the skin.

A problem with such sun care products is determining whether a product that was earlier applied is still present and providing protection from the sun. Typically, such products are formulated to be water-resistant. However, after exposure to water, and/or excessive perspiration, it is uncertain as to how much sun care product has worn off and how much remains effective on the skin. The present invention provides a solution to this problem and an easy way to determine where sunscreen or other personal care or other outdoor protection product has been removed (i.e., whether previously applied product is still present), while at the same time providing a product that is more durable and water-resistant than prior art products.

Compositions containing temporary visual indicators activated by change in pH and methods of use are known in the art. For example, U.S. Pat. No. 5,523,075 to Fuerst, et al. is directed to suncare cosmetic compositions that contain the indicator phenolphthalein which can be seen when a composition is applied to the skin and thereafter becomes colorless in response to a pH change. The pH change is mediated by an ingredient, which alters pH following application to the skin.

U.S. Pat. No. 6,531,118 to Gonzalez et al (the contents of which are incorporated herein by reference) describes topical compositions with a reversible photochromic ink for application to the skin. The photochromic ink compositions may be colorless in a non-excited state and change to color in response to ultraviolet radiation. Suncayr Inc. of Kitchener, Canada, has a website that promotes a color changing marker with ink for application to the skin of a user, which ink changes color when sunscreen is no longer protecting the user from blocking ultraviolet rays.

US Patent Application Publication 2016/0017162 (the contents of which are incorporated herein by reference) describes photochromic ink pens comprising photochromic microcapsules encapsulating photochromic dyes in resins, monomers, and polymers using standard encapsulating techniques to achieve a particle size between 300 nm and 5 microns. The publication describes in situ or interfacial polymerization using melamine resin, epoxy resin, or urea-formaldehyde to encapsulate hydrophobic, water immiscible internal phase materials in which the dye is dissolved.

Since photochromic materials often revert to their original color when the activating light is removed, other patents describe the use in photochromic compositions of components, in addition to a photochromic material, to inhibit the photochromic material from reverting to its original color, i.e., to make a color change of the photochromic material irreversible. For example, U.S. Pat. No. 8,961,897 to Faran describes the distribution within a matrix, along with a photochromic compound, of a color changing agent that reacts with the photochromic compound to form a complex capable of irreversible color change after it has been exposed to a predetermined UV radiation. The particular combination of a photochromic compound and the color changing agent compound is chosen so that the photochromic compound changes color during exposure to a predetermined dose of UV radiation, and does not revert to the original color. Other similar descriptions of photochromic ink compositions with reversible and irreversible photochromic materials are found, by way of example, in U.S. Pat. Nos. 6,132,681; 6,818,904; 5,986,273; 5,589,398; 3,787,687; 5,117,116; 4,659,649; 5,296,275; 3,903,423; 5,581,090; 6,734,440; 5,612,541; and 6,504,161; and in US Pat App Pub 2001/0019110; 2004/0109789; 2002/0022008; 2012/0137958; 2005/0285050 and 2012/0288690. The disclosures of these and the other patents and patent application publications described above and throughout this specification are incorporated herein in their entirety by reference.

None of these disclosures addresses a significant problem facing the photochromic ink compositions of the prior art, namely none of these compositions has been formulated to resist the corrosive effects of sunscreen that may be used conjointly with the photochromic ink compositions or to prevent or inhibit the compositions from being washed off when the sunscreen is washed off. What has been needed is a photochromic ink composition that has been formulated so as to have increased durability with a wide range of sunscreen products.

SUMMARY OF THE INVENTION

In accordance with the invention, there is provided a liquid or gel ink composition that satisfies the aforementioned need when matched with a selected sunscreen product or products. The ink composition has components comprising at least one photochromic pigment or dye, at least one film forming resin, and one or more solvents in which the at least one photochromic pigment or dye and the at least one film forming resin are blendable, dispersible or dissolvable, wherein the components of the ink composition are present in respective amounts such that the ink composition is in the form of a liquid or gel until evaporation of the one or more solvents and wherein, upon evaporation of the one or more solvents, the at least one film forming resin forms a film that substantially prevents the ink composition from degrading when covered with the sunscreen product and also inhibits the ink composition from washing off when the sunscreen is washed off. In a preferred embodiment of the invention, the film forming resin comprises shellac. The shellac may be combined or replaced with another film-forming resin selected, for example, from the group consisting of a polyurethane resin, an acrylic resin, silicone, and mixtures thereof. In a further preferred embodiment, the ink composition comprises a crosslinking agent in an amount effective to cause crosslinking of the film so as to render the film resistant to a wider range of sunscreen products than if the crosslinking agent were not present in the ink composition.

In accordance with one preferred embodiment of the invention, the photochromic pigment or dye is selected such that the color change is reversible. In accordance with this embodiment, the at least one reversible photochromic pigment or dye is either (a) colorless in an inactive state, activates to color when exposed to ultraviolet (UV) light, reverts to colorless when covered with the selected sunscreen product and re-activates to color when the sunscreen product is removed, or (b) an initial color in an inactive state, activates to colorless or to a different color when exposed to ultraviolet (UV) light, reverts to the initial color when covered with the selected sunscreen product and re-activates to colorless or to the different color when the sunscreen product is removed. In a preferred embodiment, the at least one pigment or dye can comprise a naphthoxazine-based photochromic dye the yields green ink when dried, but turns to a brilliant blue in the presence of sunlight.

In accordance with another preferred embodiment, the photochromic pigment or dye and the other components of the ink composition may be selected such that the color change of the at least one pigment or dye is irreversible in that the color of the photochromic pigment or dye would not reverse after it has been exposed to a predetermined amount of UV radiation. In this embodiment, an initial color of the photochromic pigment or dye can fade from a bright, activated color to a faded color after it has been exposed to a predetermined amount of UV radiation. The time period for the fade down can be calibrated to insure that, when a sunscreen product of a predetermined SPF factor is applied over the ink composition on the skin of a user who is exposed to UV light, the fade down from the activated color to the faded color occurs within a predetermined time frame, such as, e.g., about two (2) or three (3) hours, after application of the sunscreen. In this way, the fade down of the color could be used to remind the user to apply more sunscreen within the applicable time frame after application.

In yet another preferred embodiment of the invention, the at least one photochromic pigment or dye is a photochromic pigment, the solvent comprises an alcohol, and the ink composition may further comprise at least one rheology additive in an amount effective to suspend particles of the pigment in the ink composition to inhibit the pigment particles from settling. In this embodiment, the ink composition may be prepared by mixing the film forming resin, which may initially be in powder, gel or liquid form, with solvent under agitation, preferably at room temperature. The rheological additive, which may be a solid, liquid or gel, may be incorporated into the ink composition by mixing with the solvent and/or a blend of the solvent and the film forming resin in the same manner.

In a further preferred embodiment of the invention, there is provided a marker comprising the ink composition. The term marker is used herein generically to encompass a marker, pencil, crayon, stamp, stamp pad, pen, brush, roller, wipe, and/or any other dispensing device that contains the photochromic ink composition made ready for dispensation to the skin of a user. The ink composition is preferably in the form of a liquid or gel that flows smoothly from the marker so that it can easily be applied to the skin of a user where, upon evaporation of solvent, the ink composition will dry and the film forming resin will form a film to protect the photochromic pigment or dye from the selected sunscreen product. Alternatively, the ink composition can be applied by transfer to the skin from a paper material with or without a protective layer, either film or coating. Thus, as with a temporary tattoo, paper material impregnated with the ink composition may be placed face down on the skin of a user and a damp cloth or sponge may be pressed over the back of the paper material to effect transfer of the ink composition to the skin of the user. Prior to use, the paper material can have a peelable, clear plastic surface covering and protecting the ink composition. A user would peel away the peelable surface prior to applying the ink composition to his or her skin.

In yet another preferred embodiment of the invention, there is provided a system for alerting a user when to reapply sunscreen to his or her body, the system comprising any one of the liquid or gel ink compositions described above and a sunscreen product, wherein the film forming resin in the ink composition and the sunscreen product are selected such that the film produced upon evaporation of the solvent substantially prevents the ink composition from degrading when covered with the sunscreen product. In yet a further preferred embodiment, the selected sunscreen product is one that comprises the active ingredients described in any one of the eight (8) sunscreen products described in FIG. 7. In a still further preferred embodiment, the at least one film forming resin comprises shellac in an amount effective to substantially prevent the ink composition from degrading when covered with the selected sunscreen product. In the embodiments comprising a sunscreen product, the sunscreen product is preferably in the form of a lotion, a stick, a spray or an oil, and is more preferably in the form of a lotion.

In still yet another preferred embodiment of the invention, there is provided a method for alerting a user when to reapply sunscreen to his or her body, the method comprising applying any one of the aforementioned ink compositions to the skin of a user and covering the thus applied ink composition with a sunscreen product that is selected such that, upon evaporation of solvent the at least one film forming resin forms a film that substantially prevents the ink composition from degrading when covered with the sunscreen product. In a preferred embodiment, the ink composition so applied to the skin of the user will start colorless, activate to color when exposed to UV radiation, revert to colorless when covered with the sunscreen and re-activate to color when the selected sunscreen product is removed whereby to alert the user of the need to reapply the sunscreen product. Alternatively, the ink composition so applied to the skin of the user will start colored, activate to colorless when exposed to UV radiation, revert to colored when covered with the sunscreen and re-activate to colorless when the selected sunscreen product is removed whereby to alert the user of the need to reapply the sunscreen product.

BRIEF DESCRIPTION OF THE FIGURES

FIG. 1 shows Potential Film-Forming Polymers for Skin Marking Ink.
FIG. 2 shows Sunscreen Test Reagents.
FIG. 3 shows Sunscreen Resistance Spot Test Results.
FIG. 4 shows Sunscreen Test Reagents.
FIG. 5 shows Sunscreen Resistance Spot Test Results.
FIG. 6 shows Dispensing Applicator Containers.
FIG. 7 shows Label Ingredients of Coppertone Sunscreen Products.
FIG. 8 shows Polymer Binders.
FIG. 9 shows Sunscreen Products.
FIG. 10 shows Polymer Solution Samples.
FIG. 11 shows Sunscreen Resistance Test Results.
FIG. 12 shows Polymer Binders.
FIG. 13 shows Sunscreen Products.
FIG. 14 shows Photochromic Blue Ink Samples.
FIG. 15 shows Sunscreen Durability test Results—317A.
FIG. 16 shows Sunscreen Durability test Results—317B.
FIG. 17 shows Sunscreen Durability test Results—317C.
FIG. 18 shows Sunscreen Durability test Results—317D.
FIG. 19 shows Sunscreen Durability test Results—317E.
FIG. 20 shows Sunscreen Durability test Results—317F.
FIG. 21 shows Sunscreen Durability test Results—317G.
FIG. 22 shows Sunscreen Durability test Results—317H.
FIG. 23 shows Polymer Binders.
FIG. 24 shows Sunscreen Products.
FIG. 25 shows Photochromic Blue Ink Samples.
FIG. 26 shows SS Durability—Summary.
FIG. 27 shows SS Durability Test Results of 317B—Crystalac Flake 500 w/1% Oxford Blue.
FIG. 28 shows SS Durability Test Results of 319A—Crystalac Flake 500 w/1% Palatinate Purple.
FIG. 29 shows SS Durability Test Results of 319B—Crystalac Flake 500 w/0.5% Plum Red.
FIG. 30 shows SS Durability Test Results of 319C—Crystalac Flake 500 w/1% Rush Yellow.
FIG. 31 shows SS Durability Test Results of 319D—Crystalac Flake 500 w/1% Gold.
FIG. 32 shows SS Durability Test Results of 317D—SSB Komet 58 Flake w/1% Oxford Blue.
FIG. 33 shows SS Durability Test Results of 319E—SSB Komet 58 Flake w/1% Palatinate Purple.
FIG. 34 shows SS Durability Test Results of 319F—SSB Komet 58 Flake w/0.5% Plum Red.
FIG. 35 shows SS Durability Test Results of 319G—SSB Komet 58 Flake w/1% Rush Yellow.
FIG. 36 shows SS Durability Test Results of 319H—SSB Komet 58 Flake w/1% Gold.
FIG. 37 shows SS Ladder Durability Test Results of 317—Crystalac Flake 500 w/1% Rush Yellow.
FIG. 38 shows SS Ladder Durability Test Results of 317C—Summary.
FIG. 39 shows Sunscreen Products.
FIG. 40 shows Yellow Inks with Surface-Active Additives.
FIG. 41 shows Sunscreen Removal of 350 Series Yellow Inks.
FIG. 42 shows Yellow Inks with Surface-Active Additives.
FIG. 43 shows Sunscreen Removal of 350 Series Yellow Inks.
FIG. 44 shows Flexibility & Sunscreen Removal Testing of Plasticized Inks.
FIG. 45 shows Photochromatic Ink Compositions.

DETAILED DESCRIPTION

The ink composition of the present invention is formulated with a photochromic pigment or dye or blend of, a film former or blend of, a solvent or solvents, a plasticizer and pH buffer in respective amounts to enable the ink composition to be applied from a marker to the skin of a user in the form of a liquid or gel and such that, after application, the film former forms a film that protects the photochromic pigment or dye from corrosive effects of sunscreen and from washing off when the sunscreen is washed off.

The photochromic pigment or dye can comprise any of the photochromic materials and photochromic systems known in the prior art, including those described in the patents and patent publications incorporated herein by reference. In the photochromic systems used in the colorant layer, the photochromic material should be capable of undergoing color change in response to UV radiation. As used herein, the term "color change" is used to include a change from colored to colorless and vice versa, as well as a change from one color to another and a change in intensity of a color such as occurs, for example, when a vibrant color fades. The color change could be reversible or it could be irreversible, in the sense that the color change would not further change or reverse after it has been exposed to a predetermined amount of UV radiation. The irreversibility of color would remain irrespective of whether the device was exposed to visible sun radiation, held in darkness, or exposed to temperatures up to 50 degrees C.

If the color change of the photochromic dye(s) or pigment(s) is reversible, the presence or absence of color would serve as an indicator to a user as to whether sunscreen needs to be re-applied. If the color change of the photochromic dye(s) or pigment(s) is irreversible, a fade down or color change of the photochromic dye(s) or pigment(s) can be used to alert a user when to re-apply sunscreen at a predetermined time after application of sunscreen. For example, the irreversible photochromic dye or pigment can be selected such that most or all of the wavelengths of UV/VIS light absorption of the ink composition comprising the photochromic colorant falls outside of the range of sunscreen protection whereby rendering the sunscreen ineffective as a screener for the particular dye or pigment. An ink composition comprising the dye or pigment could thus predictably fade to a recognizable color within a predetermined time whether or not sunscreen is applied over the composition. In this case, the fade down would correspond to the passage of a defined period of time, such as about 2 or 3 hours, and the fade down would remind the user of the need to re-apply sunscreen. For this embodiment, one would select photochromic colorant(s) demonstrating activity in the wavelength ranges outside of the sunscreen protection ranges of roughly 285-385 nanometers. Such photochromic colorants include, by way of example, colorants commercially available from Vivimed Labs, USA Inc, 1100 Cornwall Road Suite 160, Monmouth Junction, N.J. 08852, under the trademark Reversacol™. In a preferred embodiment, the irreversible photochromic dye or pigment can be selected such that more than 50%, preferably more than 80% and most preferably more than 90 or 95% of the wavelengths of UV/VIS light absorption of the ink composition comprising the photochromic colorant falls outside of the range of sunscreen protection.

Alternatively, the ink composition comprising an irreversible photochromic dye or pigment could be paired with a sunscreen product to allow for calibration of the time period in which a fade down or color change of the photochromic dye(s) or pigment(s) occurs. In this case, the time period for fade down could be calibrated taking into consideration the concentration or sun protection factor (SPF) factor of sunscreen that is deposited atop the ink composition. This calibration would make it possible to alert a user as to a level of accumulated ultraviolet radiation striking skin to which sunscreen of a known sun protection factor has been applied over the ink composition by the fade down of the color of the pigment or dye since the sunscreen applied to the ink composition on the skin of a user would prevent the photochromic material from fading to the faded color until the predetermined time period has elapsed, e.g., about 2 or 3 hours.

It is noted that the amount and/or composition of the components that are included in the ink composition along with the photochromic material can also be adjusted to inhibit the rate of color change of the photochromic material so as to calibrate a time period in which the color of the photochromic material fades from an activated color to a faded color.

It is known to formulate cosmetic compositions, including sunscreens, with film forming agents such as shellac in combination with volatile solvents to achieve long wear and other desirable properties. For example, U.S. Pat. No. 6,620,431 and US Patent Application Publications 2015/0258010 and 2016/0208139 (the contents of which patent and patent application publications are incorporated herein by reference) describe cosmetic compositions formulated with shellac as a film former. Shellac is a natural resin excreted by the female lac insect *Kerria lacca*. The purified wax-free resin, used in the production of cosmetics, has a molecular weight of approximately 1000. It comprises a number of hydroxy-monodicarboxylic acids in the form of lactones, lactides and intramolecular esters. The principal components are aleuritic acid, shellolic acid and jalaric acid with molecular weights of 304, 296 and 280 respectively. Shellac is thus an oligomer of hyroxycarboxylic acids. By means of a solvent extraction method, e.g. using an alcohol, impurities can be removed and after decoloration with active carbon and evaporation of the alcohol, shellac can be transformed into a yellowish to faintly yellowish solid.

Shellac is graded on its acid number, which is a measure of the number of carboxylic acid groups on the shellac polymer. There are some generalities known about shellacs a function of acid number. First, the higher the acid number, the lower the pH at which dissolution of the shellac takes place. Shellac with acid numbers 68-73 dissolves at pH above 7.4. Shellac with acid numbers 74-80 dissolves at pH 7 and above. Shellac with acid numbers above 80 dissolves at pH less than 7. Second, a lower acid number provides an increased stability of the shellac while a higher acid number provides a reduced stability of the shellac. Some shellacs are refined in a bleaching process with sodium hypochlorite.

Notwithstanding its use as a film-forming agent in cosmetics and sunscreens, the inventors are unaware of any composition comprising a photochromic pigment or dye, a film forming agent and solvents in photochromic ink composition, wherein the film-forming agent comprises shellac in an amount effective to inhibit degradation of the photochromic ink composition by a sunscreen product that is applied atop the photochromic ink composition on the body of a user or that inhibits the photochromic ink composition from being washed off when the sunscreen product is washed off the body of the user. The inventors are also unaware of any formulation comprising a photochromic pigment or dye, a film-forming agent and a solvent, wherein the film forming agent has been selected to be paired with a selected sunscreen product or products such that the photochromic formulation is especially adapted to withstand the corrosive effects of the selected sunscreen product.

To provide the desirable anti-corrosive and durability effects discussed above, the ink composition of the invention may preferably comprise, by way of example, the following ingredients in the percentages described:

| % Weight | Description | Ingredient Type |
| --- | --- | --- |
| ~20-35% | Polymer/Binder/Carrier & Crosslinker | Categories 1 & 2 |
| ~55-80% | Solvents | Category 3 |
| ~<1-25% | Other Ingredients | Categories 4, 5 & 6 |

Exemplary Ingredient Categories:
1.) Polymers/Binders/Carriers—one or more of the following
   a. Acrylic/Acrylate/Methacrylate Polymers & Copolymers
   b. Carboxylated Acrylic/Acrylate/Methacrylate Polymers & Copolymers
   c. Crosslinkable Polyvinyl Carboxy Polymers & Copolymer
   d. Other Vinyl Polymers such as Polyvinylpyrrolidone
   e. Naturally-derived, Sugar-based Polymers & Copolymers, Shellacs
   f. Silicone/Siloxane Polymers & Copolymers
   g. Urethanes
2.) Crosslinkers—one or more of the following
   a. Pentaerythritol and other Polyols
   b. Siloxanes
3.) Solvent/Diluent—one or more of the following
   a. Water
   b. Organic solvent, aromatic and/or aliphatic
   c. Organic Amines, Alcohols and Acetates
   d. Organic Sulfoxides such as Dimethyl Sulfoxide (DMSO)
   e. Other Solvents such as octyldodecyl citrate crosspolymer, esters such as Glyceryl Cocoate, etc.
4.) Rheology Modifiers/Thickening Agents/Anti-Settling Agents—one or more of the following
   a. Hydrophobic Alkali Swellable Emulsion (HASE)
   b. Nonionic Polyurethane Associative Thickeners (HEUR)
   c. Clays
   d. Xanthum gum
   e. Tapioca
   f. Talcs & Other Minerals
5.) Emollients/Surfactants/Additives/Plasticizers, Etc.—one or more of the following
   a. Hydrocarbon compounds such as isododecane
   b. Silicone compounds such as dimethicone or silicone copolymers
   c. Fatty Acids, Salts of Fatty Acids
   d. pH Buffers such as Amines
   e. Plasticizers such as Methyl Epoxidized Soyate or Polyethylene Glycols of various molecular weights
6.) Color Changing Materials—one or more of the following
   a. Titanium Dioxide or other opacifying pigment
   b. Photochromic Compounds (UV light induced color change)
   c. Other Color Enhancing Compounds such as Colorants or Optical Brighteners The photochromic ink compositions shown in FIG. 45 are particularly preferred.

A preferred process for making an ink composition of the invention with the aforementioned ingredients is as follows:
Step 1: Preparation of Film-Former (Binder) Solution
1.) Add alcohol to stainless steel beaker and place on high-speed dispersator under slow agitation.
2.) Slowly add binder powder/flake ingredients with good agitation. Increase speed up to 400-500 RPM.
3.) Allow to mix until all powder/flake is dissolved.
4.) Filter and store in sealed plastic containers.
5.) Observe after 24 hours for signs of settling.
Step 2: Preparation of Photochromic Dye Solution
1.) Weigh dye powder into plastic vial using analytical balance.
2.) Slowly add solvent using analytical balance.
3.) Cap container and shake to fully mix solution.
4.) Immediately after mixing and after 24 hours, check for complete dissolution.
5.) Store in sealed plastic containers.
Step 3: Preparation of Photochromic Ink
1.) Using an analytical balance, weigh out the appropriate amount of binder solution into plastic vial.
2.) Slowly pipet the appropriate amount of dye solution into vial containing the binder solution.
3.) Stir and/or cap container and shake to fully mix solution.
4.) Store in sealed plastic containers.
5.) Observe after 24 hours for signs of settling.

The rheological modifiers/thickening agents may be included in the ink composition in an amount effective to achieve a desired viscosity and shear thinning of the ink composition, and can comprise HASE and/or surfactants and agents such as xanthan gum, hydroxyl ethyl cellulose and various other agents well known in the art. The end result is preferably a gel ink composition that flows from a roller ball pen smoothly so as to enable formation of a uniform ink line on the body of a user without starving or blobbing.

As discussed above, the ink composition will comprise a film-former/binder, which inhibits the ink composition from degrading when covered with a selected sunscreen product and/or from washing off when the sunscreen is washed off. Ink compositions comprising acrylic and polyurethane polymers will achieve this effect with certain, but not all, sunscreens, such as the Coppertone Water Babies® sunscreens, whereas ink compositions comprising shellac will achieve this effect with a wide range of sunscreens. This is described in the Examples, which follow next, which show both photochromic ink compositions of the invention and sunscreen products with which they may be paired.

Unless otherwise indicated, the photochromic dyes described herein are Reversacol™ dyes that are commercially available from Vivamed Labs USA, Inc. of Monmouth Junction, N.J., and are based on two major families of photochromic molecules: spiroxazines and naphthopyrans. These molecules achieve their color changes via a change of shape that occurs in the influence of UV light. Some members of the family can be activated by visible light, and therefore function in situations where some portion of the UV spectrum is blocked, e.g., by certain types of glass. The Reversacol™ dyes may experience a color shift when placed into a resin, based largely on steric interactions between the dye molecules and those of the surrounding matrix. If the matrix is itself too inflexible, the dyes may not exhibit their photochromic behavior. Thus a plasticizer may be added to improve flexibility of the film to allow better color shift. The shellac products Poly-Soleil SY 400™, Crystalac Premium Flake 500™, R-49 Refined Bleached Shellac™ and SSB Komet 58 Flake are commercially available from Mantrose-Haeuser Co., Inc. of Westport, Conn. The powder products are bleached. The shellac flakes are not bleached; they are refined via a melting/filtering process or solubilized in suitable solvent and decolorized with active carbon, dewaxed and filtered prior to evaporation of the solvent. The shellac is then concentrated via squeezing, drying and the like.

EXAMPLES

To determine the advantageous effects of the invention, Applicant did the following experiments.

Example 1

The market was researched for film-forming polymers used in the cosmetic and personal care industries and several selected based on their water resistance and potential sunscreen resistance. FIG. 1 lists the materials that were acquired and tried.

The powders were dissolved in solvents as per the manufacturers' recommendations, mostly denatured alcohol. Some of the samples were insoluble and films could not be made with them during this review. The Avalure, Dow, Epitex and Polysoleil polymers were soluble and formed films when cast. They were allowed to dry and then tested for their resistance to sunscreen spotting with the sunscreens listed in FIG. 2.

The films were spotted with each of the seven sunscreen test reagents for 5 minutes, then washed off with soap and water. The resulting films were evaluated for visual effect on the film surface, refer to FIG. 3. The Polysoleil SY400™ showed the best sunscreen resistance. It was then tinted with the blue photochromic dye, cast into a film and retested. The lotions showed no effect on the surface and the sprays ranged from no effect to slight effect on the surface.

The blue tinted Polysoleil ink was activated before and after sunscreen exposure and after washing the sunscreens off with soap and water. The sunscreens effectively blocked the sun and caused the ink to go colorless after application. The sunscreens were then washed off the surface with soap and water and the film reactivated in the sunlight. The spots where the spray sunscreens were applied remained colorless, but the lotion spots were reactivated showing the blue color. This indicates that the lotion sunscreens were effectively removed with soap and water. The film did not appear to be dissolved on the surface, but rather the sunscreens likely impregnated the Polysoleil film surface.

Additionally, a preliminary marker packaging trial was done to determine if the Polysoleil clear ink would wick up the polyester filaments of the markers. The tips, as well as, the marker cartridges supplied by Viscot Medical were placed in contact with the liquid ink. The clear ink wicked nicely up the tips and the cartridges.

From the above experiments, it can be seen that the film-forming polymer comprising shellac provided better results with lotion sunscreens in the above experiments than the products containing the other film-forming polymers.

Example 2

This experiment was conducted to evaluate two skin-marking ink formulations for their resistance to a variety of lotions and stick sunscreens. The varieties are sold under the COPPERTONE® brand names identified below and are commercially available.

Materials Tested:

Two skin-marking ink formulations were tested. Both inks contained the Polysoleil™ polymer; one with a blue photochromic dye (formulation no. 175A) and the second with an encapsulated pink photochromic dye (formulation no. 177B).

Sample Preparation:

The inks were applied to simulated skin sheets using sponge-tipped/dauber applicator bottles. Three sheets of each color ink were prepared for a total of 34 ink stripes/marks (17 blue and 17 pink, 3 sheets each). Samples were allowed to age overnight prior to testing.

Testing:

The ink-striped sheets were placed outdoors in natural sunlight to activate the stripes to their colors. The 17 sunscreens listed in FIG. 4 were then applied to right halves of the stripes; lotions by gloved finger and the sticks by direct application. They were allowed to set for 30 minutes then washed with hand soap and warm water to remove the sunscreens and returned outdoors for reactivation and evaluation.

Detailed Test Results:

The washed ink stripes were visually assessed for degradation and their return of original activation color. None of the sunscreens degraded or physically dissolved the ink stripes after 30-minute exposures in the sunlight. The sunscreens had little-to-no effect on the color return upon activation after sunscreens were washed off with soap and water. FIG. 5 shows sunscreen resistance spot test results.

Additionally, a marker packaging trial was done to determine if the Polysoleil™ blue and pink inks would wick up the polyester filaments of the markers. The tips, as well as, the marker cartridges supplied by Viscot Medical were placed in contact with the liquid ink. The inks wicked nicely up the tips and the cartridges.

Other dispensing methods were investigated and tried including brush bottle, sponge wand in bottle, sponge dauber bottle, other marker cartridges and roller bottle. The roller bottle and sponge dauber applied the most ink to the skin while the marker and brush the least. FIG. 6 summarizes the different applicators.

FIG. 7 describes the ingredients in the different COPPERTONE® sunscreen products.

Example 3

The following experiment was conducted to screen selective polymeric binders for their resistance to spray and lotion sunscreens.

Materials:

Four (4) shellac polymers and one (1) polyurethane polymer were included in this study as listed in FIG. 8. FIG. 9 lists the sunscreens that were used in the study.

Sample Preparation:

The shellac materials were dissolved in denatured alcohol to create 20% solutions. The shellac and polyurethane solutions were tested by themselves and at 50/50 and 75/25 shellac/PUR blends on total binder solids per FIG. 10.

The above solutions were drawn down onto plastic PVC charts using the applicators noted and allowed to dry for 2 hours under ambient conditions. The right sides of the resulting dried films were spotted with 0.3 mL each of the three sunscreens, spread by finger method to the size of a quarter and allowed to set on the samples under ambient conditions. After 1½ hours a second set of sunscreen spots were applied to the films on the left side of the charts. They were allowed to set for another 30 minutes whereby creating two sets of spots; one for a 30-minute exposure and one for a 2-hour exposure. The charts were then washed with SoftSoap® hand soap and tap water, blotted dry and visually evaluated for signs of damage.

Detailed Test Results:

The films were visually assessed for changes in appearance and film softening using a severity rating system as follows:

Severity Ratings:
5=No Effect
4=Slight Effect
3=Moderate Effect
2=Severe Effect
1=Total Failure Samples were rated using the 1 to 5 scale after 30 minutes and 2 hours. Primary failure modes observed were swelling of films, as well as, whitening.

All of the shellacs showed good resistance to the lotion sunscreens, but poor resistance to the spray sunscreen. FIG. 11 details the ratings for each binder system, along with a total score. The Crystalac Flake 500 shellac polymer showed the best performance overall with the highest score of 24 out of 30. The SSB Komet 58 Flake shellac yielded the second-best performance, similar to the Poly-Soleil SY 400. The Baycusan C 2000 showed the worst performance having considerable film softening with all sunscreens and a total score of 9. The 50/50 and 75/25 shellac/PUR blends performed somewhere in between.

An interesting combination was the 75/25 blend with Crystalac Flake 500 in that the resistance to the spray sunscreen improved. No polymer binders showed resistance to the spray sunscreens. However, it did drop in resistance to Coppertone Sport lotion. The Coppertone Kids SPF 50 spray sunscreen was the harshest sunscreen while Water Babies SPF 50 was the least aggressive.

Example 4

An experiment was done to determine the effects of extended sun exposure on prototype photochromic inks with and without sunscreen.

Materials:

Four (4) shellac polymers were tested as sole binders and at 75/25 blends (on solids) with Baycusan C 2000, polyurethane polymer. FIG. 12 lists the binders/resins and their properties. Other materials used included Reversacol™ Oxford Blue, a photochromic dye from Vivimed, and ethyl acetate. Five sunscreens were used in the study and are listed in FIG. 13.

Sample Preparation:

The Oxford Blue dye was pre-dissolved in ethyl acetate and added to the polymer solutions yielding inks having 1% photochromic dye on total binder solids. Eight (8) blue inks were made and are listed in FIG. 14.

The above inks were drawn down onto plastic PVC charts using a 0.0015" applicator and allowed to dry for 2 hours under ambient conditions. On the right sides of the resulting dried films five areas were marked off, each 3 cm×3 cm yielding 9 cm² squares. The area to the left of each square was numbered 1 through 5 corresponding to the sunscreen to be applied. The charts were photographed indoors and after sun activation outdoors.

Sunscreens were applied via microliter pipet depositing approximately 20 microliters of sunscreen in three dots within each square. The sunscreens were spread uniformly throughout each square using a gloved finger making circular motions, followed by linear up and down, then side-to-side motions. Gloved fingers were changed to prevent cross-contamination among sunscreens. They were immediately activated in the sunlight, rated, photographed and allowed to set outdoors for additional sun exposure with an irradiance level of 1.0-2.2 MED/hr and air temperature of ~50° F.

Detailed Test Results:

The charts were evaluated for color observations after 30 minutes, one hour and hourly up to 4 hours. At the conclusion of 4 hours of sunlight exposure, charts were washed using tap water, SoftSoap® hand soap and terry cloth towel. They were blotted dry with paper towel, re-activated in the sunlight and assessed for reappearance of color after sunscreen removal. Photographs were taken at each time interval.

After each time interval, the color of the control areas without sunscreen was noted, as well as, color observations of the 5 squares where sunscreens were applied. The ratings consisted of a 5-point scale as shown below. The most desirable rating with sunscreen would be a "5" indicating full blockage of sun to the blue ink underneath it.

5=No blue color
4=Slight blue color
3=Moderate blue color
2=Severe blue color, almost same as original
1=Total blue color, same as original After washing, the squares were rated again for the presence of the blue color using the scale above. As such, a rating of "1" would be most desirable to show that the color returned after the removal of sunscreen.

FIGS. 15-22 detail the ratings.

Sample 317B with the Crystalac Flake 500 yielded the best results with a bright blue activated color up to 4 hours of sunlight exposure and complete return of color after the removal of lotion sunscreens. None of the samples showed color return of Spot 1 which contained the spray sunscreen and showed varying degrees of color return in the lotion spots 2-5. Samples 317A with Poly-Soleil SY 400 and 317C with R-49 Refined Bleached Shellac turned orange in the control areas with very little return to blue in the sunscreen spots after washing. This is best illustrated in the photos.

Sample 317D with the SSB Komet 58 Flake Shellac also showed excellent properties and return of color, but wasn't as vibrant of blue as 317B.

The polyurethane modification with Baycusan C 2000 showed detrimental effects on the performance of the shellacs.

Example 5

An experiment was conducted to determine the effects of extended sun exposure on prototype photochromic inks with and without sunscreen. This study reduced the amount of sunscreen by half (0.02 uL per 18 cm² area) and includes multiple colors with top two shellac binders.

Materials:

Two (2) shellac polymers were tested as binders with five (5) photochromic dyes each dissolved in ethyl acetate. FIG. 23 lists the binders/resins and their properties. Five (5) inks were made for each shellac with the following 5 photochromic dyes; Reversacol™ Oxford Blue, Palatinate Purple, Plum Red, Rush Yellow and Gold. All except the Plum Red were incorporated at 1% load level based on solids. The Plum Red inks were made 0.5% on solids due to its poor solubility in ethyl acetate. Four (4) sunscreen lotions were used in the study and are listed in FIG. 25.

Sample Preparation:

The dyes were predissolved in ethyl acetate and added to the polymer/binder solutions yielding inks having 1% photochromic dye on total binder solids (except Plum Red at 0.5%). Ten (10) inks were made and are listed in FIG. 3. Photochromatic blue ink samples are listed FIG. 25

The above inks were drawn down onto plastic PVC charts using a 0.0015" applicator and allowed to dry for 2 hours under ambient conditions. On the right sides of the resulting dried films four areas were marked off, each 3 cm×6 cm yielding 18 cm² squares. The area to the left of each square was numbered 1 through 4 corresponding to the sunscreen to be applied. The charts were photographed indoors and after sun activation outdoors.

Sunscreens were applied via microliter pipets depositing approximately 20 microliters of sunscreen in three dots within each rectangle. The sunscreens were spread uniformly throughout each square using a gloved finger making circular motions, followed by linear up and down, then side-to-side motions. Gloved fingers were changed to prevent cross-contamination among sunscreens. They were immediately activated in the sunlight, rated, photographed and allowed to set outdoors for additional sun exposure with an irradiance level of 0.7-2.0 MED/hr and air temperature of ~50° F. The reactivation exposures were taken later in the afternoon with an irradiance level of 0.4-0.9 MED/hr.

Detailed Test Results:

The charts were evaluated for color observations after 30 minutes, one hour and after 4 hours. At the conclusion of 4 hours of sunlight exposure, charts were washed using tap water, SoftSoap® hand soap and terry cloth towel. They were blotted dry with paper towel, re-activated in the sunlight and assessed for reappearance of color after sunscreen removal. Photographs were taken at each time interval.

After each time interval, the color of the control areas without sunscreen was noted, as well as, color observations of the 4 squares where sunscreens were applied. The ratings consisted of a 5-point scale as shown below. The most desirable rating with sunscreen would be a "5" indicating full blockage of sun to the ink underneath it.

5=No color
4=Slight color
3=Moderate color
2=Severe color, almost same as original
1=Total color, same as original After washing, the squares were rated again for the presence of color using the scale above. As such, a rating of "1" would be most desirable to show that the color returned after the removal of sunscreen.

FIG. 26 summarizes the performance of each of the inks in the study while FIGS. 27-26 detail the test result ratings. Illustrative photos of the exposed samples follow the tables.

Conclusions:

Not many differences were observed between the two shellacs, except that SSB Komet 58 Flake yielded more yellowish films. The dyes showed differences in performance with Oxford Blue and Rush Yellow yielding the best balance of properties with only slight color fade after 4 hours of sunlight exposure, good blockage with the sunscreens and good color retention upon the removal of sunscreens. Both Oxford Blue and Rush Yellow yielded colorless films in the presence of visible light, but color in the presence of UV light.

It should be noted that the Plum Red yielded blue films, not purple or pink as expected.

An experiment was conducted to determine the effects of extended sun exposure on prototype photochromic ink using increasing amounts of sunscreen. Removal of sunscreen via dry wipe with terry cloth towel followed by washing with soap and water were also assessed.

Materials:

One (1) shellac polymer, Crystalac Premium Flake 500, was tested as binder with one (1) photochromic dye, Reversacol Rush Yellow predissolved in ethyl acetate, at 1% load level based on solids. Coppertone Sport Broad Spectrum SPF 50 sunscreen was used as the single lotion in this study Sample Preparation:

The photochromic ink was applied to a plastic PVC chart using a 0.0015" applicator and allowed to dry for 2 hours under ambient conditions. On the right sides of the resulting dried film four areas were marked off, each 3 cm×6 cm yielding 18 $cm^2$ squares. The area to the left of each square was labeled A through D corresponding to the amount of sunscreen to be applied. A piece of foil having the same dimensions of 3 cm×6 cm was affixed to the top of the chart to protect the photochromic dye from sun exposure. The charts were photographed indoors and after sun activation outdoors. The sunscreen was applied via microliter pipet depositing approximately 10, 20, 40 and 80 microliters of sunscreen within each rectangle. The sunscreen was spread uniformly throughout each area using a gloved finger making circular motions, followed by linear up and down, then side-to-side motions. They were immediately activated in the sunlight, rated, photographed and allowed to set outdoors for additional sun exposure with an irradiance level of 0.6-2.8 MED/hr and air temperature of ~85° F. The reactivation exposures were taken later in the afternoon with an irradiance level of 0.6-1.2 MED/hr.

Detailed Test Results:

The charts were evaluated for color observations after 30 minutes, one hour and after 4 hours. At the conclusion of 4 hours of sunlight exposure, charts were wiped with moderate pressure two times each with a fresh terry cloth towelette and reactivated, rated and photographed. They were then washed using tap water, SoftSoap hand soap and terry cloth towel, blotted dry with paper towel, re-activated in the sunlight and assessed for reappearance of color after sunscreen removal. Photographs were taken at each time interval.

After each time interval, the color of the control areas without sunscreen was noted, as well as color observations of the 4 squares where sunscreen was applied. The ratings consisted of a 5-point scale as shown below. The most desirable rating with sunscreen would be a "5" indicating full blockage of sun to the ink underneath it.

5=No color
4=Slight color
3=Moderate color
2=Severe color, almost same as original
1=Total color, same as original After dry wipe and soap and water washing, the squares were rated again for the presence of the color using the scale above. As such, a rating of "1" would be most desirable to show that the color returned after the removal of sunscreen. The foil was removed and rated for color to determine color fade of the unprotected dye as a result of sun exposure.

FIG. 37 details the ratings while FIG. 38 summarizes the results.

Conclusions:

Overall, the orange color did not fade much in 4 hours as evidenced by the foil protected unexposed area not showing much difference in color after removal. The day was partly sunny and partly cloudy.

The Coppertone Sport SPF 50 sunscreen provided excellent sunblocking at all levels for the full 4 hours, with slightly less protection at the lowest level of 10 uL. It was not easily removed by dry wipe with terry cloth towel but was completely or nearly all removed with soap and water washing.

Ink 319C appears to be well-paired for use with Coppertone Sport SPF 50 lotion sunscreen.

Example 7

Sunscreen Durability Study—Blue & Yellow Stamps & Markers

An experiment was conducted to determine the effects of extended sun exposure on prototype photochromic ink stamps and marker images with and without sunscreen. This study used 20 uL of 4 different sunscreens per 18 $cm^2$ area and included images made with the inks from rubber stamps and marker tips.

Materials:

Two (2) shellac-based inks were tested comprised of Crystalac Flake 500 shellac, denatured alcohol and photochromic dye predissolved in ethyl acetate; one blue ink containing 4% Oxford Blue and one yellow ink containing 4% Rush Yellow. Four (4) sunscreen lotions were used in the study and are listed in FIG. 39.

Sample Preparation:

The dyes were predissolved in ethyl acetate and added to the shellac solution yielding inks having 4% photochromic dye on total binder solids, 330C and 331C. The inks were applied to flexible sheet material typically used by tattoo artists to simulate skin. Two methods of application were used; ink stamp pad with rubber stamp and chisel-tipped ink marker. The inks were allowed to dry for only 5 minutes prior to application of sunscreen.

Four areas for each color were marked off as 3 cm×6 cm yielding 18 $cm^2$ rectangles. They were numbered 1 through 4 corresponding to the sunscreens to be applied. Two additional areas were made; one to set without sunscreen to determine color fade of the ink upon sunlight exposure and one to cover with foil leaving it fully protected for color comparisons at the end of exposure. The stamped and marked sheet was photographed indoors and after sun activation outdoors.

Sunscreens were applied via microliter pipets depositing approximately 20 microliters of sunscreen in three dots within each rectangle. The sunscreens were spread uniformly throughout each square using a gloved finger making circular motions, followed by linear up and down, then side-to-side motions. Gloved fingers were changed to prevent cross-contamination among sunscreens. They were immediately activated in the sunlight, rated, photographed and allowed to set outdoors for additional sun exposure with an irradiance level of 0.8-2.4 MED/hr and air temperature of ~65-70° F. The reactivation exposures were taken later in the afternoon with an irradiance level of 1.4 MED/hr.

Detailed Test Results:

The inks were fairly colorless indoors and showed bright, bold colors when activated in the sunlight. After sunscreen application, the colors did not fade much indicating insufficient blocking of the sunlight. This was likely due to too little sunscreen directly on the images because of the substrate absorbing much of the 20 microliters of sunscreen applied to each rectangle. The flexible "fake" skin was much more absorbent than the white PVC sheets used in testing full ink films. Nonetheless, the study was continued, and the images were photographed hourly up to 4 hours.

At the conclusion of 4 hours of sunlight exposure, the spots were washed using tap water, SoftSoap® hand soap and terry cloth towels. They were blotted dry with paper towel, re-activated in the sunlight and assessed for reappearance of color after sunscreen removal.

Conclusions:

Both Oxford Blue and Rush Yellow were successfully applied via rubber stamp and marker tip. They yielded fairly colorless images indoors with bright colors outdoors in the sunlight and retained good color without sunscreen for the 4-hour duration of exposure. All of the sunscreens except Tanning SPF 8 showed some color fade with both inks, the yellow more than the blue. The yellow ink showed more color fade, indicating sun-blocking, with Water Babies SPF 50 and Sport SPF 50.

All stamped and marker images were readily observed after sunscreen removal with soap and water following the 4-hours sunlight exposure.

Example 8

An experiment was conducted to evaluate surface-active agents in a skin-marking ink formulation to improve the ease of removal of a variety of COPPERTONE® brand sunscreen lotions from the dried ink surface.

Materials Tested:

Eleven different additives were formulated at their manufacturer recommended levels in one yellow skin-marking ink formulation and tested for ease of sunscreen removal. The inks contained the Crystalac Premium Flake 500 shellac polymer in ethanol with a yellow photochromic dye solution. In total, 13 samples were tested including one control having no additive, 11 inks each containing the 11 different additives and one sample containing a blend of two additives (shown in FIG. 40). Two sunscreens were used in this assessment, Coppertone Water Babies SPF 50 and Coppertone Sport SPF 50.

Sample Preparation:

The inks were made by adding the different additives to a master yellow ink Formulation 331C and mixing for five minutes on an electric mixer. They were applied to plastic PVC charts using a 0.0015" applicator and allowed to dry for 2 hours under ambient conditions. FIG. 40 lists the 13 different inks and their compatibility and appearance of ink on the charts. Not all inks were tested due to incompatibilities.

Testing:

The sheets were cut into 4 parts to be tested for six different removal methods; (1) a 300 g dry wipe with fresh terry cloth towel, (2) a 1000 g dry wipe with fresh terry cloth towel, (3) a 300 g wet wipe with fresh terry cloth towel previously soaked in tap water, (4) a 1000 g wet wipe with fresh terry cloth towel previously soaked in tap water, (5) an 80-minute distilled water immersion and (6) an 80-min tap water immersion.

On each piece, areas were marked off with 3 cm×6 cm rectangles yielding 18 cm2. The areas were marked with WB for Water Babies and SP for Sport sunscreen. The sunscreens were applied via microliter pipet depositing approximately 20 microliters of sunscreen within each rectangle. The sunscreen was spread uniformly throughout each area using a gloved finger making circular motions, followed by linear up and down, then side-to-side motions. They were immediately activated in the sunlight, photographed and allowed to set outdoors for additional 2 hours of sun exposure. They were then cleaned according to the six different methods, rated for degree of sunscreen removal according to the following:

Ratings of Sunscreen Removal

5=Complete removal, return of original color
4=Nearly all removed, return of most of the original color
3=Partial removal, return of at least half of the original color
2=Very little removal, mostly colorless, less than half of original color
1=No removal, area completely colorless Detailed Test Results:

Eight of the additives/blends were testable and at least five of them appeared to improve the sunscreen removal of the ink surfaces. FIG. 41 details the results.

Example 9

An additional five additives were tested in the same yellow ink formulation in an abbreviated experiment with COPPERTONE® brand sunscreen lotions.

Materials Tested:

Five different additives were formulated at their manufacturer recommended levels in one yellow skin-marking ink formulation and tested for ease of sunscreen removal. The inks contained the Crystalac Premium Flake 500 shellac polymer in ethanol with a yellow photochromic dye solution. In total, 6 samples were tested including one control having no additive and 5 inks each containing the 5 different additives. (shown in FIG. 42).

Two sunscreens were used in this assessment, Coppertone Water Babies SPF 50 and Coppertone Sport SPF 50.

Sample Preparation:

The inks were made by adding the different additives to a master yellow ink Formulation 331A and mixing for five minutes on an electric mixer. They were applied to plastic PVC charts using a 0.0015" applicator and allowed to dry for 2 hours under ambient conditions. FIG. 42 lists the 6 different inks and their compatibility and appearance of ink on the charts.

Testing:

The sheets were tested for one removal method, only the 300 g dry wipe with fresh terry cloth towel.

On each piece, areas were marked off with 3 cm×6 cm rectangles yielding 18 cm2. The areas were marked with WB for Water Babies and SP for Sport sunscreen. The sunscreens were applied via microliter pipet depositing approximately 20 microliters of sunscreen within each rectangle. The sunscreen was spread uniformly throughout each area using a gloved finger making circular motions, followed by linear up and down, then side-to-side motions. They were immediately activated in the sunlight, photographed and allowed to set outdoors for additional 2 hours of sun exposure. They were then cleaned by wiping with the 300 g dry method and rated for degree of sunscreen removal according to the following:

Ratings of Sunscreen Removal

5=Complete removal, return of original color
4=Nearly all removed, return of most of the original color
3=Partial removal, return of at least half of the original color
2=Very little removal, mostly colorless, less than half of original color
1=No removal, area completely colorless Detailed Test Results:

All five additives showed improvement in the removal of the Water Babies sunscreen lotion, but not the Sport lotion. FIG. 43 illustrates these results.

Example 10

An experiment was conducted to test eight different plasticizers in the yellow and blue inks in an effort to improve the flexibility of the ink with the intention of reducing cracking or flaking that might occur as the ink flexed on human skin.
Materials Tested:

Eight different plasticizers were formulated at 20% of the total using one blue and one yellow photochromic ink formulation. The inks contained the Crystalac Premium Flake 500 shellac polymer in ethanol with blue and yellow photochromic dye solutions. In total, 18 samples were tested including one control for each color having no plasticizer and 16 inks each containing the 8 different plasticizers in each ink color.
Sample Preparation:

The inks were made by adding the different plasticizers to the master blue and yellow ink formulations and mixing for five minutes on an electric mixer. They were applied to flexible sheet material typically used by tattoo artists to simulate skin using a chisel tip foam paint brush. Drawdowns of the inks were also made on PVC charts for sunscreen removal testing.
Testing:

Samples were allowed to dry for two hours then bent over a 90-degree block and rubbed slightly along the bent edges. Samples were flattened then photoactivated with an artificial sunlamp. The bent areas were observed for cracking and removal of the color ink at the bend where rubbing occurred. Ratings are as follows:
Ratings of Flexibility after 90-Degree Bend & Rub Test:
5=Very Flexible—No cracking or ink removal, complete color
4=Fairly Flexible—Slight cracking and/or ink removal, most of color is present
3=Mostly Inflexible—Moderate cracking and/or ink removal, not much color present
2=Inflexible—Severe cracking and/or ink removal, very little color present
1=Total failure with complete cracking and full ink removal, no color observed On each drawdown chart, areas were marked off with 3 cm×6 cm rectangles yielding 18 cm2. The areas were marked with WB for Water Babies and SP for Sport sunscreen. The sunscreens were applied via microliter pipet depositing approximately 20 microliters of sunscreen within each rectangle. The sunscreen was spread uniformly throughout each area using a gloved finger making circular motions, followed by linear up and down, then side-to-side motions. They were immediately activated with the sunlamp, photographed and allowed to set for an additional 2 hours of exposure. They were then cleaned by wiping with the 300 g dry method and rated for degree of sunscreen removal according to the following:
Ratings of Sunscreen Removal:
5=Complete removal, return of original color
4=Nearly all removed, return of most of the original color
3=Partial removal, return of at least half of the original color
2=Very little removal, mostly colorless, less than half of original color
1=No removal, area completely colorless Detailed Test Results:

Only one of the plasticizers improved the bend & rub test results of both of the inks; the soy ester from PolyOne called SynPlicity 1000. While it drastically improved the flexibility of the inks, the incorporation of the plasticizer reduced the sunscreen removal performance of the yellow ink. FIG. 44 details the results. It is believed that the incorporation of surface additives will improve the sunscreen removal performance.

What is claimed is:

1. An ink composition comprising at least one photochromic pigment or dye, at least one film-forming resin, and at least one solvent in which the at least one photochromic pigment or dye and the at least one film-forming resin are blendable, dispersible or dissolvable, wherein the components of the ink composition are present in respective amounts such that the ink composition is in the form of a liquid or gel until evaporation of the at least one solvent, wherein, upon evaporation of the at least one solvent, the at least one film-forming resin forms a film that (a) substantially prevents the ink composition from degrading when covered with the sunscreen product and (b) inhibits the ink composition from washing off when the sunscreen is washed off, wherein the at least one photochromic pigment or dye is an irreversible photochromic pigment or dye that fades from an initial color to a faded color within a predetermined time frame when exposed to a UV/VIS light source, the at least one photochromic pigment or dye being selected such that most or all of the wavelengths of UV/VIS light absorption of the ink composition falls outside the range of protection of a selected sunscreen product so as to render the selected sunscreen product ineffective as a screener for the at least one photochromic pigment or dye when the sunscreen product is applied over the ink composition whereby the photochromic pigment or dye will fade to the faded color in the predetermined time frame regardless of whether the select sunscreen product is applied over the ink composition with the ink composition exposed to the light source.

2. A marker comprising an ink composition comprising at least one photochromic pigment or dye, at least one film-forming resin, and at least one solvent in which the at least one photochromic pigment or dye and the at least one film-forming resin are blendable, dispersible or dissolvable, wherein the components of the ink composition are present in respective amounts such that the ink composition is in the form of a liquid or gel until evaporation of the at least one solvent, and wherein, upon evaporation of the at least one solvent, the at least one film-forming resin forms a film that (a) substantially prevents the ink composition from degrading when covered with the sunscreen product and (b) inhibits the ink composition from washing off when the sunscreen is washed off.

3. The marker according to claim 2, wherein the film-forming resin is present in the ink composition in an amount of between 20-35 wt % of the ink composition.

4. The marker according to claim 2, wherein the at least one pigment or dye comprises a dye selected from the group consisting of oxazines, naphtoxazines, spiro- naphthoxazines, pyrans, spiropyrans, napthopyrans, spironapthopyrans, fulgides, diarylethenes having heterocyclic aryl groups, dihydroindolizines, quinones, perimidine-spirocycloheadienones, viologens and mixtures thereof.

5. The marker according to claim 2, wherein the at least one pigment or dye comprises a photochromic pigment.

6. The marker according to claim 2, wherein the at least one film-forming resin comprises shellac having an acid number that is between 65-75.

7. The marker according to claim 2, wherein the film-forming resin comprises the shellac in combination with a second film-former selected from the group consisting of a polyurethane resin, a polyacrylate polymer, silicone polymer or mixtures thereof.

8. The marker according to claim 2, wherein the ink composition comprises a crosslinking agent in an amount effective to cause crosslinking of the film so as to render the film resistant to a wider range of sunscreen products than if the crosslinking agent were not present in the ink composition.

9. The marker according to claim 2, wherein the at least one photochromic pigment or dye is a reversible photochromic pigment or dye that is colorless in an inactive state, activates to color when exposed to ultraviolet (UV) light, reverts to colorless when covered with the selected sunscreen product and re-activates to color when the sunscreen product is removed.

10. The marker ink composition according to claim 2, wherein the at least one photochromic pigment or dye is a reversible photochromic pigment or dye that has an initial color in an inactive state, activates to colorless or to a different color when exposed to ultraviolet (UV) light, reverts to the initial color when covered with the selected sunscreen product and re-activates to colorless or to the different color when the sunscreen product is removed.

11. The marker according to claim 2, wherein the at least one photochromic pigment or dye is a photochromic pigment, the at least one solvent comprises an alcohol or other, and the ink composition further comprises at least one rheology additive in an amount effective to suspend particles of the pigment in the ink composition to inhibit the pigment particles from settling.

12. The marker according to claim 2, wherein the marker is in the form of a pencil, crayon, stamp, stamp pad, pen, brush, roller or wipe.

13. A system comprising the ink composition according to claim 1 and a sunscreen product.

14. The system according to claim 13, wherein the sunscreen product is in the form of a lotion, a stick, a spray or an oil.

15. A method for alerting a user when to reapply sunscreen to his or her body, the method comprising applying the ink composition of claim 1, to the skin of a user and covering the thus applied ink composition with a sunscreen product that is selected such that, upon evaporation of solvent the at least one film-forming resin forms a film that substantially prevents the ink composition from degrading when covered with the sunscreen product, wherein the film-forming resin comprises shellac in an amount effective substantially to prevent the sunscreen product from degrading the ink composition.

16. The ink composition according to claim 1, wherein the ink composition comprises the following components and amounts:

| | |
|---|---|
| photochromic colorant | 1.0-2.0 wt % |
| film-forming resin | 20-30 wt % |
| solvent | 50-65 wt %; and |
| other components | 10-25 wt %. |

17. The ink composition according to claim 1, wherein the film-forming resin comprises shellac which renders the ink composition more resistant to the sunscreen product than a film-forming resin consisting of polyurethane or polyacrylate.

18. A marker comprising the ink composition according to claim 1.

* * * * *

(12) EX PARTE REEXAMINATION CERTIFICATE (12544th)
United States Patent
Levine et al.

(10) Number: US 11,655,383 C1
(45) Certificate Issued: Mar. 20, 2024

(54) PHOTOCHROMIC COMPOSITIONS, MARKERS CONTAINING THE SAME, AND SYSTEMS AND METHODS FOR THEIR USE

(71) Applicant: JADS INTERNATIONAL LLC, Lutherville, MD (US)

(72) Inventors: Andrew Seth Levine, Lutherville, MD (US); Nicole Ann Zujovic, Baltimore, MD (US); Debora Hense, Plymouth, MI (US)

Reexamination Request:
No. 90/015,257, Jul. 11, 2023

Reexamination Certificate for:
Patent No.: 11,655,383
Issued: May 23, 2023
Appl. No.: 16/279,125
Filed: Feb. 19, 2019

Related U.S. Application Data

(63) Continuation-in-part of application No. PCT/US2017/047751, filed on Aug. 21, 2017.

(60) Provisional application No. 62/377,033, filed on Aug. 19, 2016.

(51) Int. Cl.
| | |
|---|---|
| C09D 11/17 | (2014.01) |
| A61K 8/72 | (2006.01) |
| A61K 8/81 | (2006.01) |
| A61K 8/87 | (2006.01) |
| A61Q 1/02 | (2006.01) |
| C09D 11/50 | (2014.01) |
| G01N 21/29 | (2006.01) |

(52) U.S. Cl.
CPC ............. *C09D 11/17* (2013.01); *A61K 8/72* (2013.01); *A61K 8/8152* (2013.01); *A61K 8/87* (2013.01); *A61Q 1/025* (2013.01); *C09D 11/50* (2013.01); *A61K 2800/438* (2013.01); *G01N 21/29* (2013.01)

(58) Field of Classification Search
None
See application file for complete search history.

(56) References Cited

To view the complete listing of prior art documents cited during the proceeding for Reexamination Control Number 90/015,257, please refer to the USPTO's Patent Electronic System.

*Primary Examiner* — Alan D Diamond

(57) ABSTRACT

An ink composition including at least one photochromic pigment or dye, at least one film-forming resin, and at least one solvent in which the at least one photochromic pigment or dye and the at least one film-forming resin are dispersible or dissolvable, wherein the components of the ink composition are present in respective amounts such that the ink composition is in the form of a liquid or gel until evaporation of the at least one solvent, and wherein, upon evaporation of the at least one solvent, the at least one film-forming resin forms a film that (a) inhibits the irk composition from degrading when covered with the sunscreen product or (b) inhibits the ink composition from washing off when the sunscreen is washed off or both, the film-forming resin including shellac, polyurethane, acrylic polymer, silicone polymer or a mixture thereof.

| Product | Description | Form | Manufacturer |
|---|---|---|---|
| Avalure Flex-6 Polymer | Polyurethane | Powder | Lubrizol |
| Dow MQ-1640 | Trimethylsiloxy silicate & Polypropyl Silsesquioxane | Flake Resin | Dow Corning |
| Epitex 66 | Polyacrylate Emulsion | White Liquid | Dow Chemical Co. |
| Polysoleil SY400 | Shellac | Powder | Mantrose-Haeuser Co. |
| Silsoft Gel | Silicone | Gel | Momentive |
| Silsoft ETS | Ethyl Trisiloxane | Clear Liquid | Momentive |

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 6 is cancelled.

Claims 2 and 7 are determined to be patentable as amended.

Claims 3-5 and 8-12, dependent on an amended claim, are determined to be patentable.

Claims 1 and 13-18 were not reexamined.

2. A marker comprising an ink composition comprising at least one photochromic pigment or dye, at least one film-forming resin, and at least one solvent in which the at least one photochromic pigment or dye and the at least one film-forming resin are blendable, dispersible or dissolvable, wherein the components of the ink composition are present in respective amounts such that the ink composition is in the form of a liquid or gel until evaporation of the at least one solvent, and wherein, upon evaporation of the at least one solvent, the at least one film-forming resin forms a film that (a) substantially prevents the ink composition from degrading when covered with the sunscreen product and (b) inhibits the ink composition from washing off when the sunscreen is washed off, *wherein the at least one film-forming resin comprises shellac having an acid number that is between 65-75.*

7. [The marker according to claim 2] *A marker comprising an ink composition comprising at least one photochromic pigment or dye, at least one film-forming resin, and at least one solvent in which the at least one photochromic pigment or dye and the at least one film-forming resin are blendable, dispersible or dissolvable, wherein the components of the ink composition are present in respective amounts such that the ink composition is in the form of a liquid or gel until evaporation of the at least one solvent, and wherein, upon evaporation of the at least one solvent, the at least one film-forming resin forms a film that (a) substantially prevents the ink composition from degrading when covered with the sunscreen product and (b) inhibits the ink composition from washing off when the sunscreen is washed off*, wherein the film-forming resin comprises [the] shellac in combination with a second film-former selected from the group consisting of a polyurethane resin, a polyacrylate polymer, silicone polymer or mixtures thereof.

* * * * *